(12) United States Patent
Madison et al.

(10) Patent No.: US 8,293,542 B2
(45) Date of Patent: Oct. 23, 2012

(54) REAL TIME BINDING ANALYSIS OF ANTIGENS ON A BIOSENSOR SURFACE

(75) Inventors: Lara Madison, Bridgewater, MA (US); John Gerstenmaier, Belmont, MA (US)

(73) Assignee: X-Body, Inc., Waltham, MA (US)

( * ) Notice: Subject to any disclaimer, the term of this patent is extended or adjusted under 35 U.S.C. 154(b) by 420 days.

(21) Appl. No.: 12/402,629

(22) Filed: Mar. 12, 2009

(65) Prior Publication Data

US 2009/0176658 A1 Jul. 9, 2009

Related U.S. Application Data

(60) Division of application No. 11/290,036, filed on Nov. 30, 2005, now Pat. No. 7,524,625, which is a continuation-in-part of application No. 10/399,940, filed on Jan. 16, 2004, now Pat. No. 7,202,076, which is a continuation of application No. PCT/US01/45455, filed on Oct. 23, 2001, which is a continuation-in-part of application No. 09/930,352, filed on Aug. 15, 2001, now Pat. No. 7,094,595, said application No. 11/290,036 is a continuation-in-part of application No. PCT/US03/01298, filed on Jan. 16, 2003, which is a continuation of application No. 10/059,060, filed on Jan. 28, 2002, now Pat. No. 7,070,987, which is a continuation-in-part of application No. 09/930,352, filed on Aug. 15, 2001, now Pat. No. 7,094,595, which is a continuation-in-part of application No. PCT/US03/01298, filed on Jan. 16, 2003, which is a continuation-in-part of application No. 10/058,626, filed on Jan. 28, 2002, now Pat. No. 6,951,715, which is a continuation-in-part of application No. 09/930,352, filed on Aug. 15, 2001, now Pat. No. 7,094,595.

(60) Provisional application No. 60/244,312, filed on Oct. 30, 2000, provisional application No. 60/283,314, filed on Apr. 12, 2001, provisional application No. 60/303,028, filed on Jul. 3, 2001.

(51) Int. Cl.
*G01N 33/563* (2006.01)

(52) U.S. Cl. ...... 436/512; 422/82.11; 435/7.5; 436/518; 436/524; 436/525; 436/805

(58) Field of Classification Search .................. None
See application file for complete search history.

(56) References Cited

U.S. PATENT DOCUMENTS

| | | |
|---|---|---|
| 4,815,843 A | 3/1989 | Tiefenthaler |
| 4,882,288 A | 11/1989 | North et al. |
| 5,071,248 A | 12/1991 | Tiefenthaler |
| 5,216,680 A | 6/1993 | Magnusson et al. |
| 5,492,840 A * | 2/1996 | Malmqvist et al. ........ 436/518 |
| 5,554,541 A * | 9/1996 | Malmqvist et al. ........ 436/518 |
| 5,666,197 A | 9/1997 | Guerra |
| 5,738,825 A | 4/1998 | Rudigier |
| 6,218,194 B1 | 4/2001 | Lyndin et al. |
| 6,346,376 B1 | 2/2002 | Sigrist et al. |
| 6,395,558 B1 | 5/2002 | Duveneck |
| 6,756,078 B2 | 6/2004 | Bookbinder |
| 6,771,376 B2 | 8/2004 | Budach et al. |
| 6,787,110 B2 | 9/2004 | Tiefenthaler |
| 6,867,869 B2 | 3/2005 | Budach et al. |
| 6,870,630 B2 | 3/2005 | Budach et al. |
| 6,990,259 B2 | 1/2006 | Cunningham |
| 7,064,844 B2 | 6/2006 | Budach et al. |
| 7,158,230 B2 | 1/2007 | Cunningham |
| 7,162,125 B1 | 1/2007 | Schulz |
| 7,197,198 B2 | 3/2007 | Schulz |
| 7,267,993 B2 | 9/2007 | Pentrenko |
| 7,396,675 B2 | 7/2008 | Pawlak et al. |
| 7,479,404 B2 | 1/2009 | Cunningham |
| 7,483,127 B1 | 1/2009 | Li |
| 7,497,992 B2 | 3/2009 | Cunningham |
| 7,521,769 B2 | 4/2009 | Cunningham |
| 7,524,625 B2 | 4/2009 | Madison |
| 7,534,578 B1 | 5/2009 | Baird |
| 7,620,276 B2 | 11/2009 | Schulz |
| 7,628,005 B2 | 12/2009 | Schaeffler |
| 7,742,662 B2 | 6/2010 | Cunningham |
| 7,756,365 B2 | 7/2010 | Cunningham |
| 7,790,406 B2 | 9/2010 | Cunningham |
| 2002/0028045 A1 | 3/2002 | Yoshimura |
| 2002/0028480 A1 | 3/2002 | Maher |
| 2002/0127565 A1 | 9/2002 | Cunningham |
| 2002/0168295 A1 | 11/2002 | Cunningham |

(Continued)

FOREIGN PATENT DOCUMENTS

EP 1031828 8/2000

(Continued)

OTHER PUBLICATIONS

Wawro et al., "Optical fiber endface biosensor based on resonances in dielectric waveguide gratings", Biomedical Diagnostic Guidance and Surgical-Assist Systems II, Vo-Dihn et al. eds., Proceedings of SPIE, vol. 3911 (2000), p. 86-94.

Office Action dated Apr. 2, 2007 for U.S. Appl. No. 11/506,639 (now U.S. Patent No. 7,298,477).

U.S. Appl. No. 60/244,312, filed Oct. 30, 2000.

U.S. Appl. No. 60/283,314, filed Apr. 12, 2001.

U.S. Appl. No. 60/303,028, filed Jul. 3, 2001.

Peng et al., "Resonant scattering from two-dimensional gratings", J. Opt. Soc. Am. A., vol. 13, No. 5, p. 993-1005, 1996.

Magnusson, et al., "New principle for optical filters", Appl. Phys. Lett. 61 (9), p. 1022-1024, 1992.

Peng, et al., "Experimental demonstration of resonant anomalies in diffraction from two-dimensional gratings", Optics Letters, vol. 21, No. 8, p. 549-551, 1996.

(Continued)

*Primary Examiner* — Chris L Chin
(74) *Attorney, Agent, or Firm* — McDonnell Boehnen Hulbert & Berghoff LLP

(57) ABSTRACT

The invention provides methods for detecting interactions between phage and antigen or antigen and antibody using biosensors.

14 Claims, 15 Drawing Sheets

U.S. PATENT DOCUMENTS

| | | |
|---|---|---|
| 2003/0017580 A1 | 1/2003 | Cunningham |
| 2003/0017581 A1 | 1/2003 | Li |
| 2003/0026891 A1 | 2/2003 | Qiu |
| 2003/0027327 A1 | 2/2003 | Cunningham |
| 2003/0027328 A1 | 2/2003 | Cunningham |
| 2003/0032039 A1 | 2/2003 | Cunningham |
| 2003/0059855 A1 | 3/2003 | Cunningham |
| 2003/0068657 A1 | 4/2003 | Lin |
| 2003/0077660 A1 | 4/2003 | Pien |
| 2003/0092075 A1 | 5/2003 | Pepper |
| 2003/0104479 A1 | 6/2003 | Bright |
| 2003/0113766 A1 | 6/2003 | Pepper |
| 2004/0005540 A1 | 1/2004 | Pentrenko et al. |
| 2004/0091397 A1 | 5/2004 | Picard |
| 2004/0132172 A1 | 7/2004 | Cunningham |
| 2004/0132214 A1 | 7/2004 | Lin |
| 2004/0151626 A1 | 8/2004 | Cunningham |
| 2004/0219619 A1 | 11/2004 | Fernandez-Salas |
| 2004/0229215 A1 | 11/2004 | Pentrenko et al. |
| 2005/0214803 A1 | 9/2005 | Wang |
| 2006/0003372 A1 | 1/2006 | Li |
| 2006/0275825 A1 | 12/2006 | Baird et al. |
| 2007/0015210 A1 | 1/2007 | Ezekiel |
| 2008/0213910 A1 | 9/2008 | Jogikalmath |
| 2008/0219892 A1 | 9/2008 | Cunningham |
| 2008/0240543 A1 | 10/2008 | Budach |
| 2008/0299673 A1 | 12/2008 | Wagner et al. |
| 2009/0017488 A1 | 1/2009 | Binder et al. |
| 2009/0130703 A1 | 5/2009 | Wagner et al. |
| 2009/0137422 A1 | 5/2009 | Laing et al. |
| 2009/0148955 A1 | 6/2009 | Cunningham |
| 2009/0176658 A1 | 7/2009 | Madison |
| 2009/0179637 A1 | 7/2009 | Cunningham |
| 2009/0192049 A1 | 7/2009 | Baird et al. |
| 2009/0227469 A1 | 9/2009 | Conklin |
| 2009/0264314 A1 | 10/2009 | Cunningham |
| 2009/0269244 A1 | 10/2009 | Cunningham |
| 2009/0282931 A1 | 11/2009 | Laing |
| 2009/0305304 A1 | 12/2009 | Laing et al. |
| 2010/0003743 A1 | 1/2010 | Schulz |
| 2010/0008826 A1 | 1/2010 | Schulz |
| 2010/0015721 A1 | 1/2010 | Laing |
| 2010/0043571 A1 | 2/2010 | Laing |
| 2010/0143959 A1 | 6/2010 | Cunningham |
| 2010/0195099 A1 | 8/2010 | Rockney |
| 2010/0196925 A1 | 8/2010 | Genick |
| 2010/0202923 A1 | 8/2010 | Cunningham |
| 2010/0227769 A1 | 9/2010 | Schulz |
| 2010/0231907 A1 | 9/2010 | Pien |
| 2010/0291575 A1 | 11/2010 | Shamah |

FOREIGN PATENT DOCUMENTS

| | | |
|---|---|---|
| EP | 1085315 | 3/2001 |
| JP | 05211871 | 8/1993 |
| WO | WO 96/38726 | 12/1996 |
| WO | 0020591 | 4/2000 |
| WO | WO 01/02839 | 1/2001 |
| WO | WO 01/79559 | 10/2001 |
| WO | WO 01/92870 | 12/2001 |
| WO | 0236177 | 5/2002 |
| WO | WO 02/061429 A2 | 8/2002 |
| WO | WO 03/065041 A1 | 8/2003 |
| WO | 03/074548 | 9/2003 |
| WO | 2005001475 | 1/2005 |
| WO | 2007/064702 | 6/2007 |
| WO | 2009/009718 | 1/2009 |
| WO | 2010005600 | 1/2010 |
| WO | 2010/075033 | 7/2010 |

OTHER PUBLICATIONS

International Search Report for PCT/US2006/045684 for corresponding PCT application dated Apr. 12, 2007.

Cekaite, et al., "Analysis of the humoral immune response to immunoselected phage-displayed peptides by a microarray-based method", Proteomics 2004, 4, 2572-2582.

Sun, et al., "Use of bioluminescent *Salmonella* for assessing the efficiency of contructed phage-based biosorbent", Journal of Industrial Microbiology & Biotechnology (2000) 25, 273-275.

Wan, et al., "Landscape phage-based magnetostrictive biosensor for detecting *Bacillus anthracis* spores", Proceedings of IEEE Sensors, 2005, 1308-1311.

Cooper, "Current biosensor technologies in drug discovery", Drug Discovery World Summer 2006, pp. 68-82.

Comley, "Label-Free Detection New biosensors facilitate broader range of drug discovery applications", Drug Discovery World Winter 2004/5, pp. 63-74.

Cunningham, "Colorimetric Resonant Reflection as a Direct Biochemical Assay Technique", IEEE, Annual International Conference on Micro Electro Mechanical Systems, MEMS, 2002. Las Vegas, NV Jan. 20-24, 2002.

Palmer, "Diffraction Gratings, The Crucial Dispersive Component", Spectroscopy, 10(2), pp. 14-15 (1995).

Bandell et al., "Noxious Cold Ion Channel TRPA1 is Activated by Pungent Compounds and Bradykinin" Neuron, vol. 41, pp. 849-957 (2004).

Cunningham et al., "Label-Free Assays on the BIND System", Journal of Biomolecular Screening, 9:481 (2004).

Ramsden et al., "Optical Method for Measurement of Number and Shape of Attached Cells in Real Time", Cytometry, vol. 19, pp. 97-102 (1995).

Li et al., "Measurement of Adhesion and Spreading Kinetics of Baby Hamster Kidney and Hybridoma Cells Using an Integrated Optical Method", Biotechnol. Prog., vol. 10, pp. 520-524 (1994).

Takeda et al., "The Integrins", Genome Biology, 8:215 (2007).

Sancho et al., "Binding kinetics of monomeric and aggregated IgG to Kupffer cells and hepatocytes of mice", Immunology, 53:283 (1984).

Chaplen et al., "Improvement of Bioactive Compound Classification through Integration of Orthogonal Cell-Based Biosensing Methods",Sensor, 7:38-51 (2007).

U.S. Appl. No. 13/166,936, filed Jun. 23, 2011.

Machine translation of JP 05-211871.

* cited by examiner

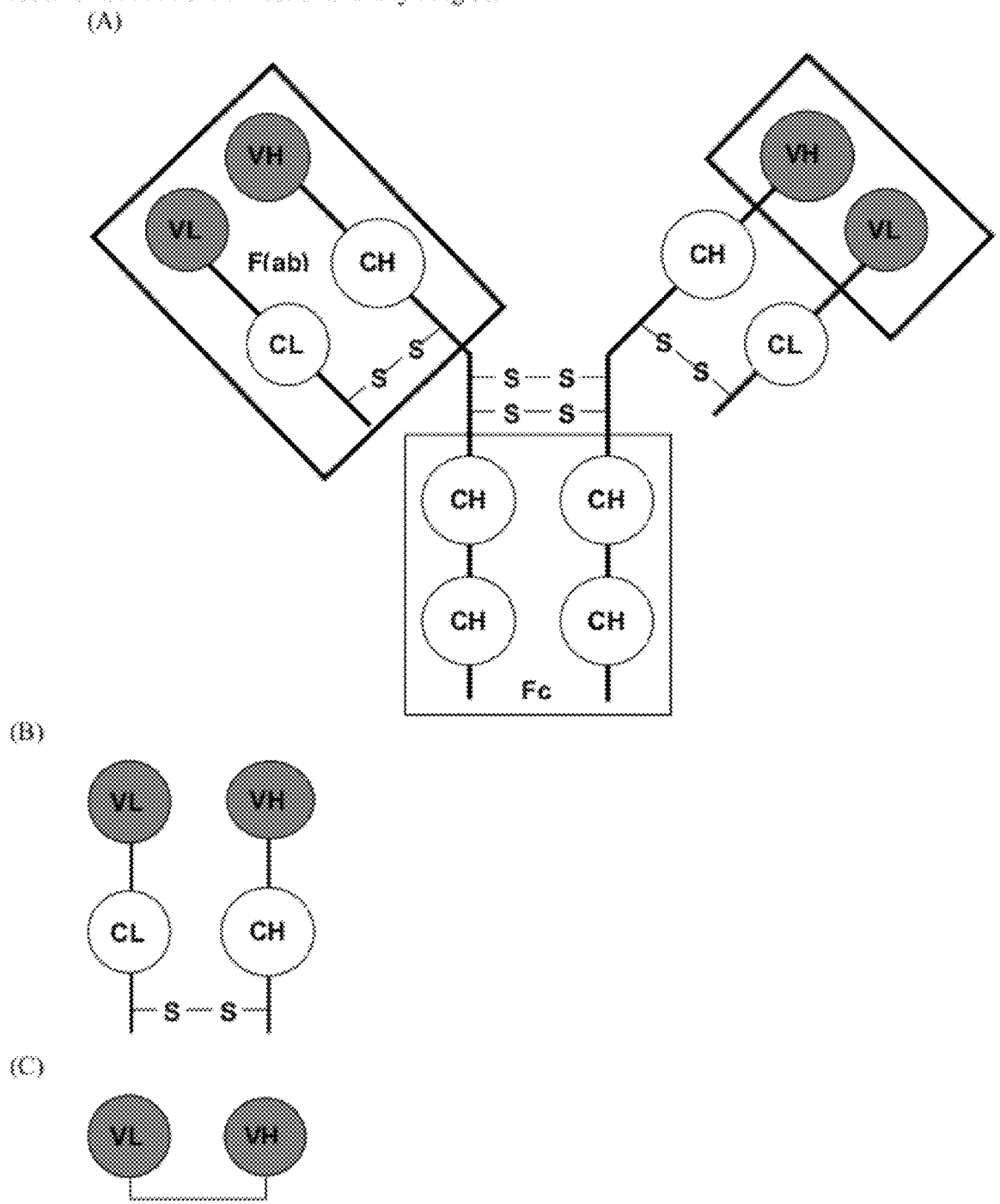
Figure 1: (A) a full IgG and antibody domains, (B) F(ab) and (C) scFv where V stands for variable, C stands for constant, H stands for heavy chain, L stands for light chain, and S-S stands for a disulfide bond. In the case of (C) the line between the VL and VH is a recombinant linker not found naturally in IgGs.

Figure 2: Titration of bacterial viruses on GA3 BIND® Biosensor

| N=2 | Concentration of phage (pfu/ml) | Shift (nm) | SD | %CV |
|---|---|---|---|---|
| Stock phage in 20% glycerol were diluted in to 20 % glycerol | 1.0e14 | 5.285 | 0.008 | 0.16 |
| | 3.3e13 | 4.027 | 0.006 | 0.15 |
| | 1.1e13 | 2.518 | 0.083 | 3.3 |
| | 3.6e12 | 1.052 | 0.066 | 6.3 |
| | 1.2e12 | 0.400 | 0.037 | 9.3 |
| | 4.0e11 | 0.150 | 0.004 | 2.8 |
| | 1.3e11 | 0.036 | 0.005 | 12.7 |
| Stock phage in 20% glycerol were diluted in PBS | 1.0c14 | 5.440 | 0.038 | 0.71 |
| | 3.3e13 | 4.215 | 0.001 | 0.03 |
| | 1.1e13 | 2.523 | 0.145 | 5.7 |
| | 3.6e12 | 1.128 | 0.035 | 3.1 |
| | 1.2e12 | 0.488 | 0.048 | 9.9 |
| | 4.0e11 | 0.150 | 0.008 | 5.1 |
| | 1.3e11 | 0.038 | 0.007 | 19.6 |

Figure 3: Comparison of capture of F(ab) spiked into PBS and periplasmic extracts prepared from *Escherichia coli*

(A) Creation of the sF(ab) specific capture surface and the capture of the sF(ab)

| Sample | Delta PWV | SD | %CV | N |
|---|---|---|---|---|
| Protein A | 0.336 | 0.016 | 4.9 | 48 |
| 1% Milk | 0.661 | 0.023 | 3.4 | 48 |
| Rabbit anti-mouse F(ab')2 | 0.799 | 0.039 | 4.9 | 48 |
| 0.33 ug/ml sFab in PBS | 0.066 | 0.014 | 18.5 | 3 |
| 1.0 ug/ml sFab in PBS | 0.150 | 0.010 | 6.3 | 3 |
| 3.0 ug/ml sFab in PBS | 0.211 | 0.008 | 3.5 | 3 |
| 0.33 ug/ml sFab in Periplasmic Extract | 0.110 | 0.005 | 4.8 | 3 |
| 1.0 ug/ml sFab in Periplasmic Extract | 0.172 | 0.012 | 6.4 | 3 |
| 3.0 ug/ml sFab in Periplasmic Extract | 0.238 | 0.009 | 3.6 | 3 |

(B) Graphical representation of the capture of sFab recorded in Figure (A)

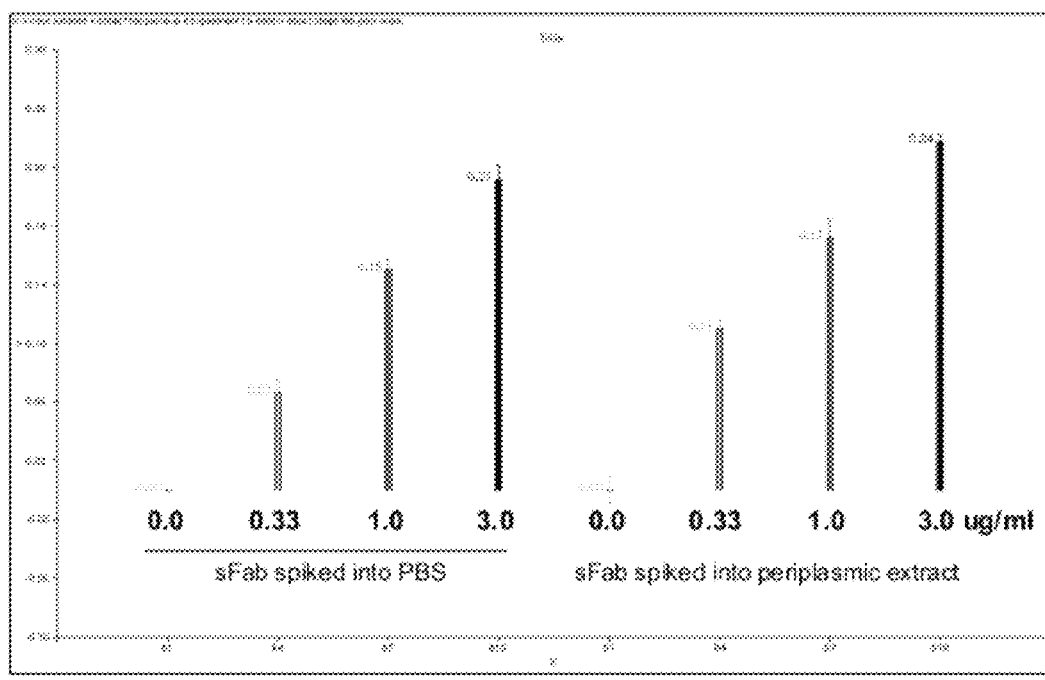

Figure 4 A-B: ScFv capture from periplasmic extract on a TIO BIND® Biosensor (A) Creation of the sF(ab) specific capture surface and the capture of the scFv containing a 6xHis and c-myc tag.

| Sample | Shift | SD | CV% | N |
|---|---|---|---|---|
| Protein A | 0.629 | 0.020 | 3.1 | 96 |
| Milk | 0.945 | 0.019 | 2.0 | 96 |
| Rabbit anti-mouse-FC | 0.712 | 0.070 | 9.8 | 96 |
| Anti-His & Anti-cmyc | 0.652 | 0.021 | 3.2 | 48 |
| Anti-cmyc | 0.653 | 0.018 | 2.8 | 48 |

(B) Capture of purified scFv spiked into PBS and Periplasmic extract.

| Purified scFv spiked into PBS (n = 3) | | | | | | |
|---|---|---|---|---|---|---|
| scFv (5 ug/ml) | Mixture capture Ab | | | Anti-cmyc capture Ab | | |
| | Shift (nm) | SD | %CV | Shift (nm) | SD | %CV |
| #1 | 0.051 | 0.007 | 13.7 | 0.238 | 0.116 | 49 |
| #2 | 0.256 | 0.005 | 1.9 | 0.241 | 0.017 | 7.1 |
| #3 | 0.148 | 0.006 | 4.1 | 0.104 | 0.006 | 5.6 |
| #4 | 0.131 | 0.008 | 6.4 | 0.123 | 0.017 | 13.5 |
| #5 | 0.281 | 0.012 | 4.2 | 0.212 | 0.005 | 2.4 |
| Purified scFv spiked into periplasmic extract (n=3) | | | | | | |
| scFv (5 ug/ml) | Mixture capture Ab | | | Anti-cmyc capture Ab | | |
| | Shift (nm) | SD | %CV | Shift (nm) | SD | %CV |
| #1 | 0.231 | 0.006 | 2.5 | 0.201 | 0.017 | 8.5 |
| #2 | 0.250 | 0.004 | 1.6 | 0.228 | 0.030 | 13.3 |
| #3 | 0.146 | 0.002 | 1.2 | 0.078 | 0.021 | 27 |
| #4 | 0.102 | 0.005 | 5.2 | 0.033 | 0.016 | 48 |
| #5 | 0.447 | 0.006 | 1.3 | 0.395 | 0.003 | 0.8 |

Figure 4 C-D
(C) Graphical representation of the capture of scFv recorded in (B)
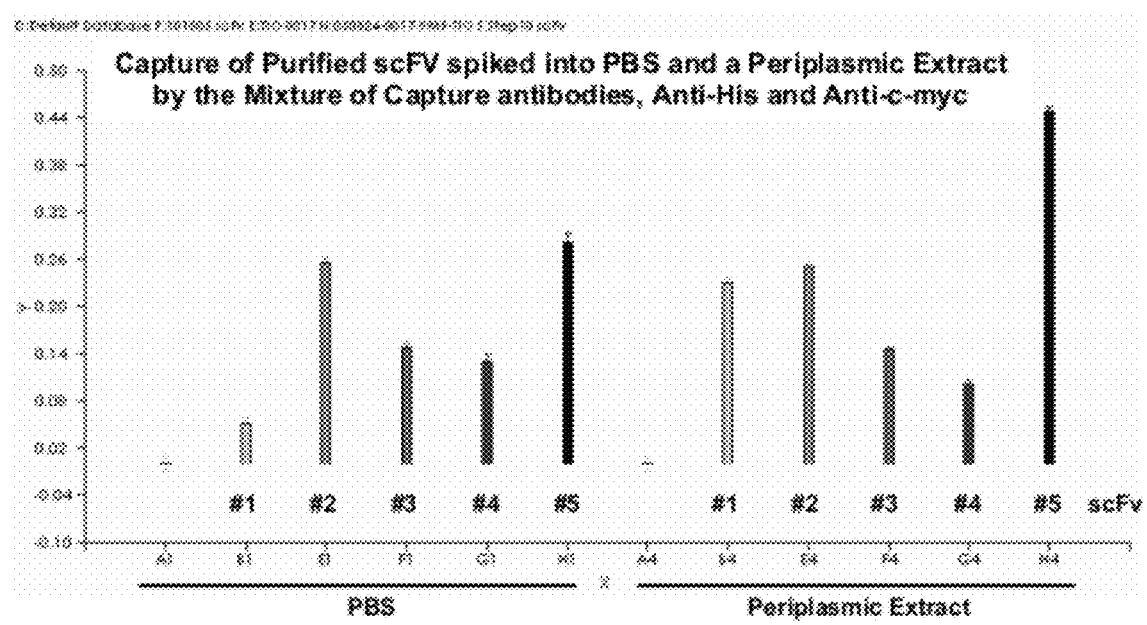
(D) Graphical representation of the capture of scFv recorded in (B)
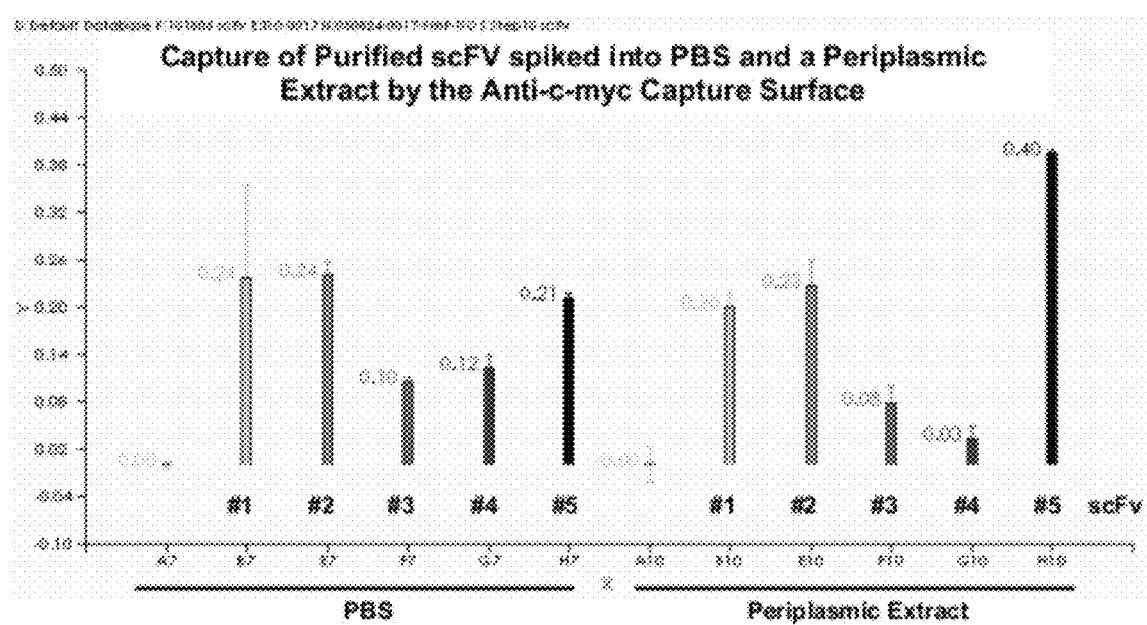

Figure 5 A-C: ScFv capture from periplasmic extract on a SA1 BIND® Biosensor (A) Creation of the surface and specific capture of scFv

|  | Shift | SD | CV% |
|---|---|---|---|
| Biotin anti-His | 2.290 | 0.053 | 2.3 |

(B) Capture of scFv spiked into PBS and periplasmic culture

| scFv 8 ug/ml | PBS | | | Periplasmic extract | | | N |
|---|---|---|---|---|---|---|---|
| | Shift | SD | CV% | Shift | SD | CV% | |
| #1 | 0.104 | 0.010 | 9.4 | 0.16 | 0.004 | 2.2 | 3 |
| #2 | 0.091 | 0.004 | 4.2 | 0.33 | 0.017 | 5.1 | 3 |
| #3 | 0.065 | 0.004 | 6.2 | 0.17 | 0.006 | 3.5 | 3 |
| #4 | 0.087 | 0.004 | 4.8 | 0.19 | 0.012 | 6.1 | 3 |

(C) Graphical representation of scFv capture of purified scFv spiked into PBS and Periplasmic Extract

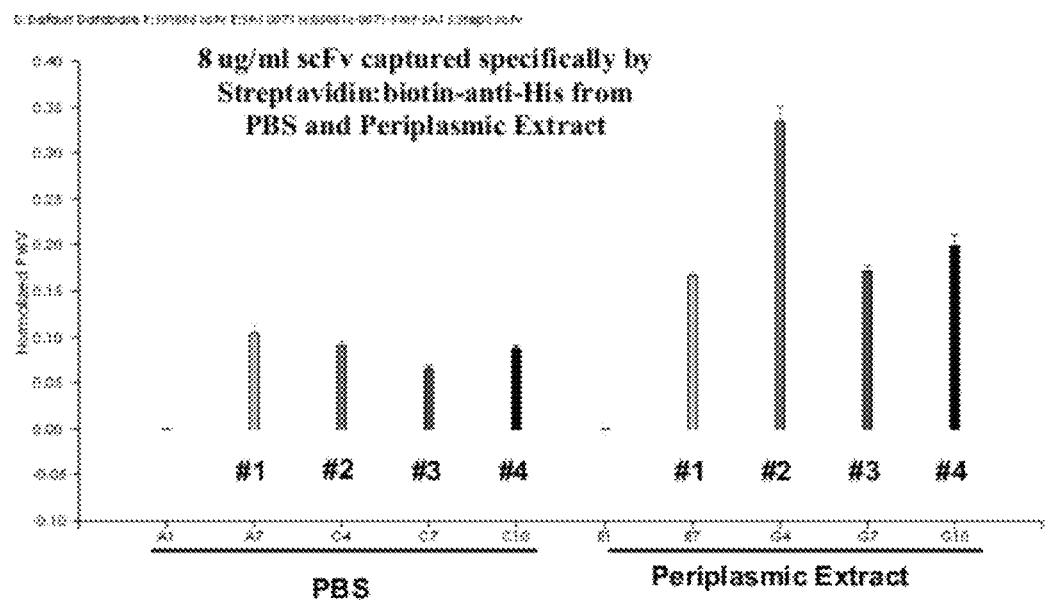

Figure 6A-C: ScFv capture from periplasmic extract on a GA1 BIND® Biosensor
(A) Creation of scFv capture surface
|  | Shift | SD | CV% |
|---|---|---|---|
| Anti-c-myc | 1.247 | 0.013 | 1.1 |
(B) Capture of purified scFv spiked into PBS and a periplasmic extract
| ScFv (5 ug/ml) | PBS | | | Periplasmic extract | | | N |
|---|---|---|---|---|---|---|---|
|  | Shift | SD | CV% | Shift | SD | CV% |  |
| #1 | 0.169 | 0.003 | 1.5 | 0.107 | 0.001 | 1.2 | 3 |
| #2 | 0.182 | 0.017 | 9.5 | 0.180 | 0.005 | 2.6 | 3 |
| #3 | 0.155 | 0.005 | 3.0 | 0.125 | 0.005 | 4.4 | 3 |
| #4 | 0.182 | 0.005 | 2.9 | 0.118 | 0.005 | 4.4 | 3 |
| #5 | 0.154 | 0.003 | 1.9 | 0.229 | 0.031 | 13.4 | 3 |
| #6 | 0.173 | 0.011 | 6.3 | 0.144 | 0.011 | 7.4 | 3 |
(C) Graphical representation of scFv capture from PBS and Periplasmic Extract
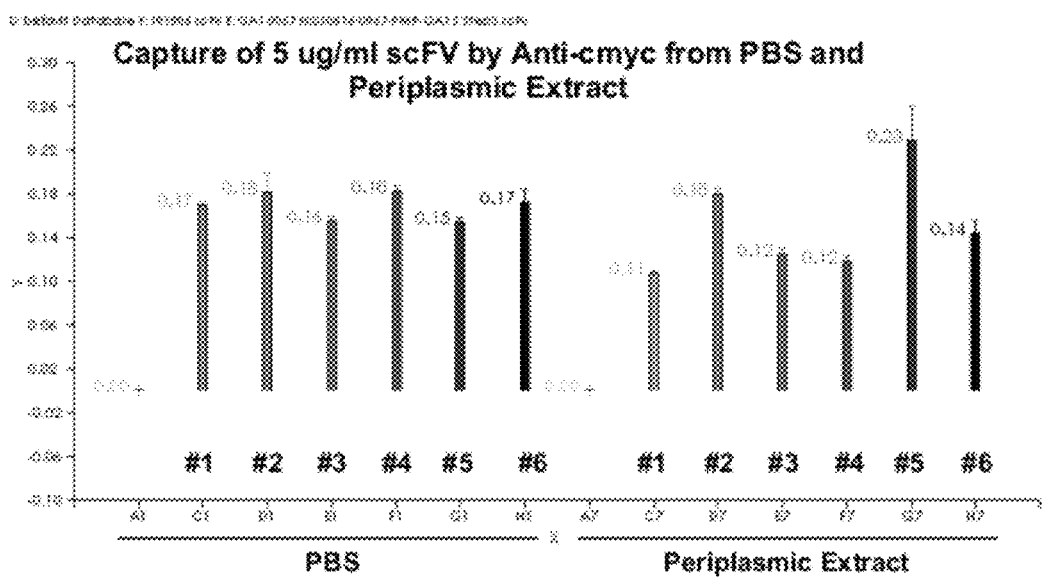

Figure 7 A-C: Capture of IgGs from hybridoma supernatants using an anti-Fc TIO BIND® Biosensor (A) Creation of specific IgG capture surface

| Plate 15 N = 96 | ProteinA | 1% Milk | Rabbit anti-mouse-Fc | Rabbit IgG Block |
|---|---|---|---|---|
| Shift (nm) | 0.484 | 0.944 | 0.931 | 0.080 |
| SD | 0.017 | 0.014 | 0.050 | 0.017 |
| CV% | 3.5 | 1.5 | 5.3 | 20.9 |

(B) Creation of specific IgG capture surface

| Plate 16 N = 96 | ProteinA | 1% Milk | Rabbit anti-mouse-Fc | Rabbit IgG Block |
|---|---|---|---|---|
| Shift (nm) | 0.491 | 0.940 | 0.927 | 0.090 |
| SD | 0.016 | 0.017 | 0.054 | 0.026 |
| CV% | 3.2 | 1.8 | 5.8 | 28.8 |

(C) Capture of IgGs from hybridoma media.

|  | Plate15 (N=2) | | | Plate 16 (N=1) |
|---|---|---|---|---|
| Ab-# | Shift | SD | %CV | Shift |
| 22 | 0.531 | 0.124 | 23.3 | 0.385 |
| 25 | 0.908 | 0.174 | 19.1 | 0.983 |
| 26 | 1.130 | 0.096 | 8.5 | 1.199 |
| 28 | 1.189 | 0.143 | 12.0 | 0.933 |
| 30 | 1.384 | 0.195 | 14.1 | 1.549 |
| 31 | 0.744 | 0.141 | 19.0 | 0.388 |
| 32 | 0.929 | 0.026 | 2.8 | 0.867 |
| 33 | 1.208 | 0.094 | 7.8 | 1.362 |
| 34 | 1.372 | 0.062 | 4.5 | 1.473 |
| 35 | 1.164 | 0.086 | 7.4 | 1.556 |
| 36 | 1.411 | 0.066 | 4.7 | 1.017 |
| 37 | 0.919 | 0.077 | 8.4 | 1.256 |

Figure 7D-E (D) Graphical representation of antigen, antigen + cells, and cells binding to the IgGs captured on the biosensor surface.

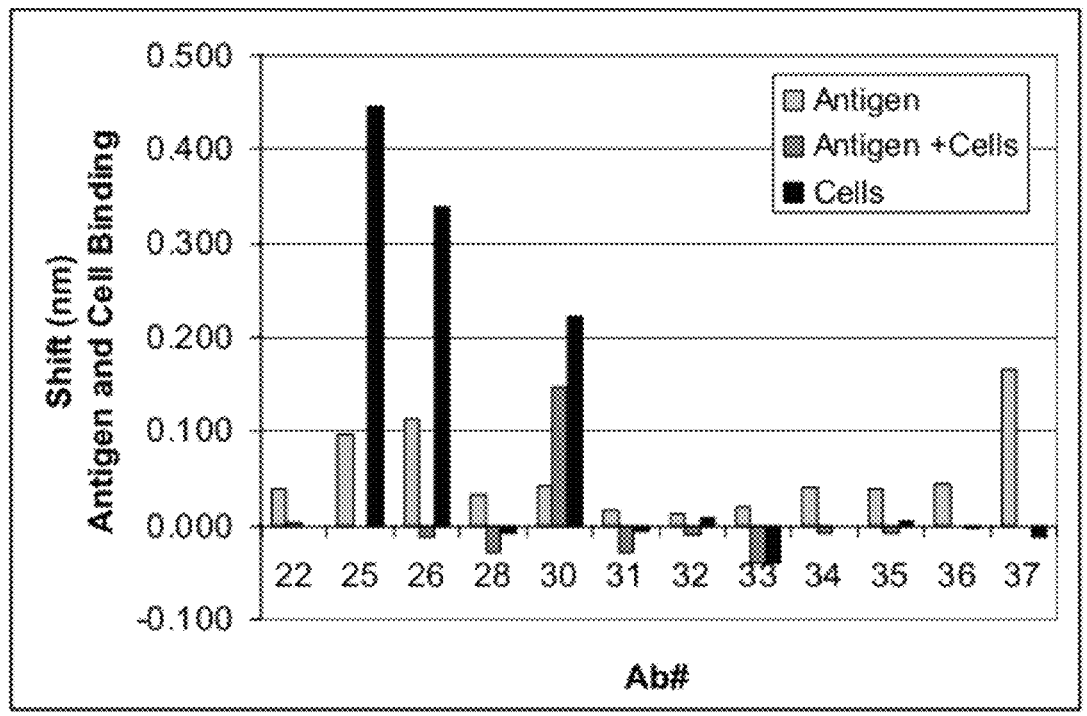

(E) Tabular representation of antigen, antigen + cells, and cells binding to the IgGs captured on the biosensor surface with the normalization of this binding to the amount of IgG captured on the biosensor surface.

| | Shift (nm) | | | Ratio | | |
|---|---|---|---|---|---|---|
| Ab # | Antigen | Antigen + Cells | Cells | Ag/IgG | Antigen + Cells /IgG | Cells/IgG |
| 22 | 0.039 | 0.003 | 0.001 | 0.10 | 0.01 | 0.00 |
| 25 | 0.096 | 0.000 | 0.445 | 0.10 | 0.00 | 0.49 |
| 26 | 0.115 | -0.013 | 0.339 | 0.10 | 0.01 | 0.30 |
| 28 | 0.033 | -0.030 | 0.008 | 0.04 | 0.02 | 0.01 |
| 30 | 0.043 | 0.148 | 0.223 | 0.03 | 0.11 | 0.16 |
| 31 | 0.017 | -0.028 | 0.006 | 0.04 | 0.04 | 0.01 |
| 32 | 0.013 | -0.010 | 0.008 | 0.02 | 0.01 | 0.01 |
| 33 | 0.020 | -0.039 | 0.040 | 0.01 | 0.03 | 0.03 |
| 34 | 0.041 | -0.008 | 0.001 | 0.03 | 0.01 | 0.00 |
| 35 | 0.039 | -0.007 | 0.005 | 0.02 | 0.01 | 0.00 |
| 36 | 0.045 | -0.001 | 0.003 | 0.04 | 0.00 | 0.00 |
| 37 | 0.167 | -0.001 | 0.012 | 0.13 | 0.00 | 0.01 |

Figure 8 A-C: IgG capture from serum using an anti-Fc TIO BIND® Biosensor.(N=2)

(A) Creation of a specific IgG binding surface

|  | Shift | SD | %CV |
|---|---|---|---|
| ProteinA | 0.450 | 0.061 | 13.5 |
| 1% Milk | 0.963 | 0.031 | 3.2 |
| Anti-Fc | 0.697 | 0.099 | 14.2 |

(B) Capture of IgGs from Serum

| [M IgG] (ug/ml) | 0% Serum | | | 5% Serum | | | 10% Serum | | |
|---|---|---|---|---|---|---|---|---|---|
|  | Shift | SD | %CV | Shift | SD | %CV | Shift | SD | %CV |
| 0 | 0.000 | 0.018 | 0.0 | 0.000 | 0.011 | 0.0 | 0.000 | 0.002 | 0.0 |
| 0.1 | -0.011 | 0.021 | -196.6 | 0.052 | 0.018 | 35.5 | 0.010 | 0.014 | 142.0 |
| 0.2 | 0.002 | 0.017 | 983.6 | 0.046 | 0.029 | 63.2 | 0.017 | 0.005 | 28.2 |
| 0.4 | 0.039 | 0.052 | 132.8 | 0.073 | 0.029 | 40.2 | 0.051 | 0.015 | 29.0 |
| 0.8 | 0.083 | 0.037 | 44.2 | 0.128 | 0.025 | 19.5 | 0.110 | 0.002 | 1.7 |
| 1.6 | 0.247 | 0.015 | 5.9 | 0.240 | 0.000 | 0.1 | 0.225 | 0.043 | 19.2 |
| 3.2 | 0.344 | 0.006 | 1.8 | 0.289 | 0.003 | 1.0 | 0.279 | 0.011 | 3.8 |
| 6.4 | 0.447 | 0.027 | 6.0 | 0.340 | 0.021 | 6.1 | 0.308 | 0.001 | 0.4 |

(C) Capture of IgGs from Serum

| [MIgG] (ug/ml) | 20% Serum | | | 40% Serum | | | 100% Serum | | |
|---|---|---|---|---|---|---|---|---|---|
|  | Shift | SD | %CV | Shift | SD | %CV | Shift | SD | %CV |
| 0 | 0.000 | 0.016 | 0.0 | 0.000 | 0.003 | 0.0 | 0.000 | 0.003 | 0.0 |
| 0.1 | 0.008 | 0.003 | 31.8 | 0.009 | 0.005 | 58.8 | 0.017 | 0.013 | 77.1 |
| 0.2 | 0.042 | 0.017 | 40.0 | 0.018 | 0.006 | 33.1 | 0.040 | 0.008 | 19.0 |
| 0.4 | 0.066 | 0.011 | 16.1 | 0.046 | 0.004 | 9.3 | 0.064 | 0.020 | 31.9 |
| 0.8 | 0.109 | 0.034 | 31.6 | 0.086 | 0.019 | 22.5 | 0.103 | 0.029 | 28.6 |
| 1.6 | 0.183 | 0.019 | 10.2 | 0.154 | 0.033 | 21.2 | 0.170 | 0.024 | 14.0 |
| 3.2 | 0.220 | 0.014 | 6.1 | 0.194 | 0.019 | 9.8 | 0.211 | 0.011 | 5.3 |
| 6.4 | 0.312 | 0.015 | 4.8 | 0.249 | 0.026 | 10.6 | 0.235 | 0.010 | 4.4 |

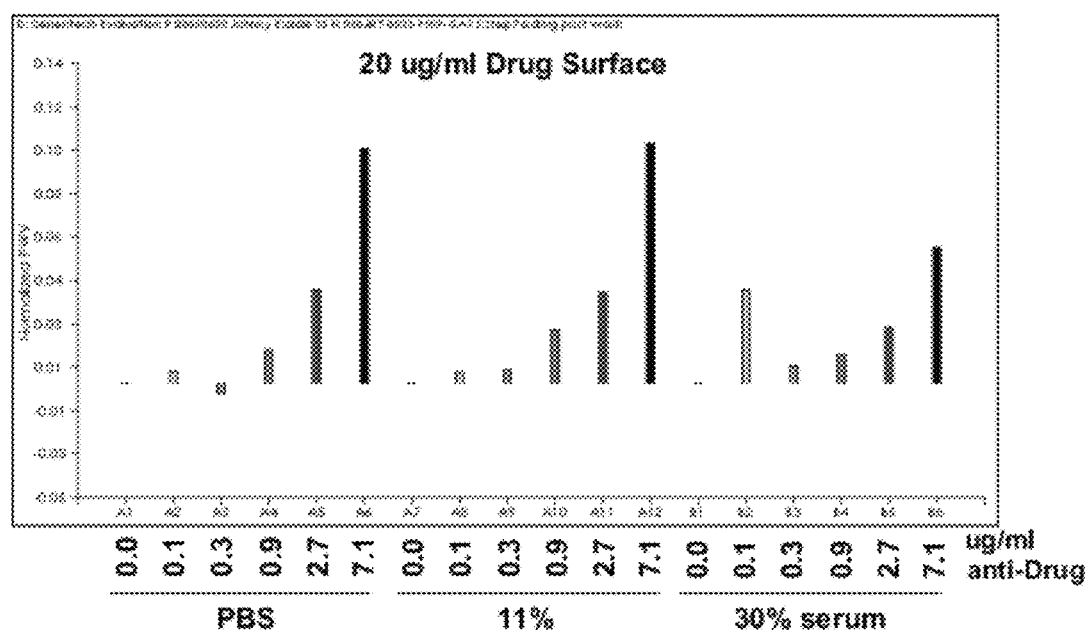
Figure 9 A-B: Drug : Anti-Drug Assay in serum using a GAI BIND® Biosensor
(A) Creation of a specific surface for the capture of the IgG
| Drug is an IgG | 20 ug/ml Drug (N=48) | 20 ug/ml Drug plus Rabbit IgG (N=48) | 0 Drug Plus Rabbit IgG (N=48) | 20 ug/ml Drug; Rabbit IgG; START (N=12) | 0 ug/ml Drug; Rabbit IgG; START (N=12) |
|---|---|---|---|---|---|
| Shift (nm) | 0.364 | 0.496 | 0.773 | 1.523 | 1.605 |
| SD | 0.032 | 0.022 | 0.033 | 0.085 | 0.033 |
| CV% | 8.8 | 4.4 | 4.2 | 5.6 | 2.0 |
(B) Capture of the anti-drug from PBS, 11% and 30% serum on the 20ug/ml Drug surface.

(C) Capture of the anti-drug from PBS, 11% and 30% serum on the 0ug/ml Drug surface.

Figure 10 A-B: IgG capture from Serum using an anti-Fc TIO BIND® Biosensor.
(A) Creation of the Drug surface for the capture of anti-Drug
| N = 96 | ProteinA | 1% Milk | Rabbit anti-human-Fc | Rabbit IgG Block | 50 ug/ml Drug |
|---|---|---|---|---|---|
| Shift (nm) | 0.447 | 0.976 | 0.805 | 0.029 | 0.805 |
| SD | 0.029 | 0.019 | 0.082 | 0.010 | 0.082 |
| CV% | 6.5 | 2.0 | 10.2 | 34.1 | 10.2 |
(B) Capture of the anti-drug from PBS, 11% and 30% serum.
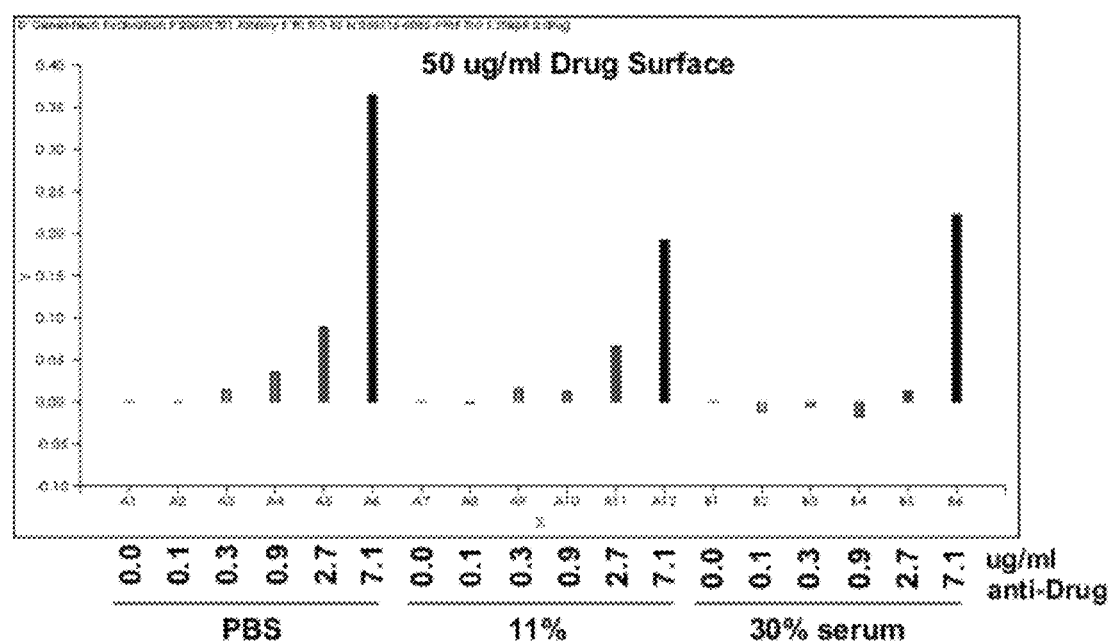

(C) Capture of the anti-drug from PBS, 11% and 30% serum on the 0ug/ml Drug surface.

Figure 11 A-D: Endpoint analysis of antibody binning and identification of sandwich pairs of antibodies on an anti-Fc TIO BIND® Biosensor (A) Creation of IgG specific surface

| N = 96 | ProteinA | 1% Milk | Rabbit anti-mouse-Fc | Rabbit IgG Block | Mouse IgG Block |
|---|---|---|---|---|---|
| Shift (nm) | 0.488 | 1.040 | 0.789 | 0.116 | 0.422 |
| SD | 0.017 | 0.019 | 0.061 | 0.033 | 0.019 |
| CV% | 3.5 | 1.8 | 7.7 | 28.6 | 4.5 |

(B) Capture of Layer 1 (Antibody)

| N = 8 | Ab-1 | Ab-2 | Ab-3 | Ab-4 |
|---|---|---|---|---|
| Shift (nm) | 0.281 | 0.219 | 0.324 | 0.293 |
| SD | 0.011 | 0.005 | 0.10 | 0.010 |
| CV% | 4.0 | 2.2 | 3.1 | 3.5 |

(C) Capture of Layer 2 (Antigen by Antibody)

| N = 4 | Ab-1 | Ab-2 | Ab-3 | Ab-4 |
|---|---|---|---|---|
| Shift (nm) | 0.173 | 0.206 | 0.207 | 0.046 |
| SD | 0.005 | 0.001 | 0.004 | 0.003 |
| CV% | 2.9 | 0.7 | 2.1 | 6.0 |
| Antigen Shift / Antibody Shift (Affinity) | 0.35 | 0.56 | 0.38 | 0.01 |

(D) Capture of Layer 3 (Antibody by Antibody-Antigen Complex)

| N = 1 | Ab-1 | Ab-2 | Ab-3 | Ab-4 |
|---|---|---|---|---|
| Ab-1 | 0.016 | 0.150 | 0.024 | 0.005 |
| Ab-2 | 0.138 | 0.063 | 0.203 | -0.009 |
| Ab-3 | 0.033 | 0.212 | 0.050 | -0.004 |
| Ab-4 | -0.009 | 0.017 | -0.012 | -0.015 |

REAL TIME BINDING ANALYSIS OF ANTIGENS ON A BIOSENSOR SURFACE

PRIORITY

This application is a divisional application of U.S. Ser. No. 11/290,036, filed Nov. 30, 2005, (now allowed), which claims priority to U.S. Ser. No. 10/399,940, filed Jan. 16, 2004, now U.S. Pat. No. 7,202,076, which is a continuation of PCT/US01/45455, filed Oct. 23, 2001, which is a continuation in part of U.S. Ser. No. 09/930,352, filed Aug. 15, 2001, now U.S. Pat. No. 7,094,595, which claims the benefit of U.S. Ser. No. 60/303,028 filed Jul. 3, 2001; U.S. Ser. No. 60/283,314, filed Apr. 12, 2001; and U.S. Ser. No. 60/244,312, filed Oct. 30, 2000. U.S. Ser. No. 11/290,036, filed Nov. 30, 2005, also claims priority to PCT/US03/01298, filed Jan. 16, 2003, which is a continuation of U.S. Ser. No. 10/059,060, filed Jan. 28, 2002, now U.S. Pat. No. 7,070,987, which is a continuation in part of U.S. Ser. No. 09/930,352, filed Aug. 15, 2001, now U.S. Pat. No. 7,094,595. U.S. Ser. No. 11/290,036, filed Nov. 30, 2005, also claims priority to PCT/US03/01298, filed Jan. 16, 2003, which is a continuation in part of U.S. Ser. No. 10/058,626, filed Jan. 28, 2002, which is continuation in part of U.S. Ser. No. 09/930,352, filed Aug. 15, 2001, now U.S. Pat. No. 7,094,595, all of which are incorporated herein by reference in their entirety.

FIELD OF THE INVENTION

The invention relates to the field of biosensors and methods comprising detecting antigens that specifically bind to an antibody, antibody fragment, or phage.

BACKGROUND OF THE INVENTION

The ability to detect binding between phage and mammalian cells is an essential component for discovery of therapeutic and diagnostic antibodies. A typical pipeline for identifying potential therapeutic and diagnostic antibodies includes: (1) phage display and phage panning experiments on soluble protein or cellular associated proteins (in the soluble form or expressed on cells); (2) a phage ELISA performed on soluble protein (for cellular targets—a peptide or protein-mimic of the cellular associated protein); (3) the display gene in the phage genome is subcloned via molecular biology techniques to a soluble antibody fragment expressing plasmid; (4) The antibody fragment then is expressed and purified; (5) once purified the antibody fragment can be tested for cellular functional binding in ELISA, FACS, Guava or FMAT; (6) The lead antibody fragment is analyzed for binding kinetics; and (7) the top antibody lead is then cloned into a full antibody expression vector for large scale production, kinetic analysis and in vivo efficacy models.

Typical assays for analysis of functional binding of phage to protein targets associated with cells include whole mammalian or bacterial cell enzyme-linked immunosorbent assay (ELISA), flow cytometry (Fluorescence Activated Cell Sorter, FACS), Guava microcytometry products (Guava Technologies, Hayward, Calif.), and fluorescence microassay technology (FMAT). ELISAs have high background binding of phage, because cells are complex and phages have a tendency to bind non-specifically. Background binding in ELISA is intensified due to amplification of the binding signal. Cellular ELISAs are also difficult due to the need of many washes between steps, which is cumbersome if the cells are non-adherent as a centrifugal spin is required between each wash. Often adherent cells must be fixed in order to keep the cells attached to the ELISA plate during washes, either manually or on a plate washer. The fixation can change the natural epitopes of the protein on cells. Phage binding in FACs and Guava is also difficult, because each phage clone needs to be purified to get enough phage for a signal.

Currently, most researchers spend a lot of time and effort in cloning the display on the phage to fragments and/or full IgGs in order to investigate the functional binding to cells. The more time spent identifying potential therapeutic antibodies, the longer it takes to get effective therapeutic antibodies into medical clinics. Thus, there is a need in the phage display field for a quick route to identifying functional binding of antibodies to mammalian cells.

SUMMARY OF THE INVENTION

One embodiment of the invention provides a method of detecting binding of a binding partner to a phage. The method comprises immobilizing a crude phage preparation, unconcentrated phage preparation, non-homogenous phage preparation, or a combination thereof on a biosensor and contacting the biosensor with the binding partner. Binding of the binding partner to a phage immobilized on the biosensor is detected. The binding partner can be a small molecule, a carbohydrate, a polymer, a peptide, a soluble protein, a cellular receptor, an antigen mimic of a cellular receptor, a cell, a mammalian cell, or a mammalian cell surface protein. The phage preparation and antigen do not necessarily comprise a detectable label. The phage preparation can be a phage display library. The phage preparation can be passively immobilized to the biosensor or can be immobilized to the biosensor by an antibody specific for a phage coat protein. The antibody or antibody fragment can be immobilized to the biosensor by binding to a protein that is bound to the biosensor. If the antibody or antibody fragment comprises a tag, the antibody or antibody fragment can be immobilized to the biosensor by antibodies specific for the tag. The biosensor can be a calorimetric resonant reflectance biosensor or an evanescent wave-based biosensor.

Another embodiment of the invention provides a method for determining epitope classes of antibodies in an antibody population. The method comprises immobilizing a display phage, antibody, or antibody fragment to a biosensor and contacting the biosensor with a binding partner that specifically binds to the display phage, antibody, or antibody fragment immobilized to the biosensor, under conditions suitable for binding of the binding partner to the display phage, antibody, or antibody fragment. The antibody population is contacted with the biosensor. A detectable signal generated by binding of the antibody population to the binding partner indicates that different epitope classes are present in the antibody population than in the immobilized display phage, antibody, or antibody fragment. The antibody population, binding partner and immobilized display phage, immobilized antibody, or immobilized antibody fragment do not necessary comprise a detectable label. The antibody population can comprise phage clones, antibody fragments, full antibodies, phage displaying a full antibody, phage displaying an antibody fragment, antibodies from a hybridoma, and antibodies from a phage display screen. The display phage can be a purified phage preparation, a crude phage preparation, an unconcentrated phage preparation, or a non-homologous phage preparation. The binding partner can be a small molecule, a carbohydrate, a polymer, a peptide, a soluble protein, a cellular receptor, an antigen mimic of a cellular receptor, a mammalian cell, or a mammalian cell surface protein. The mammalian cell surface protein can be a membrane-associated protein, a single transmembrane protein, a multi-transmembrane protein, or a protein channel. The biosensor can be a calorimetric resonant reflectance biosensor or an evanescent wave-based biosensor.

Therefore, the invention provides methods to, e.g., resolve low concentrations of binding partners, rank protein affinities, work with samples comprising complex mixtures, and perform off-rate ranking analysis.

BRIEF DESCRIPTION OF THE DRAWINGS

FIG. 1A-C depicts an antibody and antibody fragments, F(ab) and scFv. FIG. 1A shows a full IgG antibody and domains of the IgG. FIG. 1B shows F(ab). FIG. 1C shows scFv.

FIG. 2 shows titration of bacterial viruses on GA3 BIND® Biosensor

FIG. 3A-B shows F(ab) capture from periplasmic extract on a TIO BIND® Biosensor. FIG. 3A shows creation of the sF(ab) specific capture surface and the capture of sF(ab). FIG. 3B shows a graphical representation of the capture of sFab recorded in FIG. 3A.

FIG. 4A-D shows scFv capture from periplasmic extract on a TIO BIND® Biosensor. FIG. 5A shows the creation of scFv specific capture surface and capture of scFv containing a 6×His and c-myc tag. FIG. 4B shows capture of purified scFv spiked into PBS and periplasmic extract. FIG. 4C shows a graphical representation of capture of scFv recorded in FIG. 4B. FIG. 4D shows graphical representation of capture of scFv recorded in FIG. 4B.

FIG. 5A-C shows scFv capture from periplasmic extract on a SA1 BIND® Biosensor. FIG. 5A shows creation of the specific capture surface for proteins expressing a 6×his tag. FIG. 5B shows capture of scFv spiked into PBS and periplasmic culture. FIG. 5C shows graphical representation of scFv capture of purified scFv spiked into PBS and periplasmic extract.

FIG. 6A-C shows scFv capture from periplasmic extract on a GA1 BIND® Biosensor. FIG. 6A shows creation of specific capture surface for proteins containing a c-myc tag. FIG. 6B shows capture of purified scFv spiked into PBS and a periplasmic extract. FIG. 6C shows a graphical representation of scFv capture from PBS and periplasmic extract.

FIG. 7A-E shows capture of IgGS from hybridoma supernatants using an anti-Fc TIO BIND® Biosensor. FIG. 7A shows creation of specific mouse IgG capture surface. FIG. 7B shows creation of specific mouse IgG capture surface. FIG. 7C shows capture of IgGs from hybridoma media. FIG. 7D shows a graphical representation of antigen, antigen and cells, and cells binding to the IgGs captured on the biosensor surface. FIG. 7E shows a tabular representation of antigen, antigen and cells, and cells binding to the IgGs captured on the biosensor surface with the normalization of this binding to the amount of IgG captured on the biosensor surface.

FIG. 8A-C shows IgG capture from serum using an anti-Fc TIO BIND® Biosensor. FIG. 8A shows creation of a specific mouse IgG binding surface. FIG. 8B shows capture of IgGs from serum. FIG. 8C shows capture of IgGs from serum.

FIG. 9A-C shows a drug—anti-drug assay in serum using a GA1 BIND® Biosensor. FIG. 9A shows creation of a surface for the capture of an IgG, an anti-drug. FIG. 9B shows capture of the anti-drug from PBS, 11% and 30% serum on the 20 ug/ml drug surface. FIG. 9C shows capture of the anti-drug from PBS, 11% and 30% serum on the 0 ug/ml drug surface.

FIG. 10A-C shows IgG capture from serum using an anti-Fc TIO BIND® Biosensor. FIG. 10A shows creation of the drug surface for the capture of anti-drug. FIG. 10B shows capture of the anti-drug from PBS, 11% and 30% serum on the 50 ug/ml Drug surface. FIG. 10C shows capture of the anti-drug from PBS, 11% and 30% serum on the 0 ug/ml drug surface.

FIG. 11A-D shows endpoint analysis of antibody binning and identification of sandwich pairs of antibodies on an anti-FC TIO BIND® Biosensor. FIG. 11A shows creation of mouse IgG specific surface. FIG. 11B shows capture of layer 1 (Antibody). FIG. 11C shows capture of layer 2 (Antigen by Antibody). FIG. 11D shows capture of layer 3 (Antibody by Antibody-Antigen Complex).

DETAILED DESCRIPTION OF THE INVENTION

Biosensors

Figure 9C:
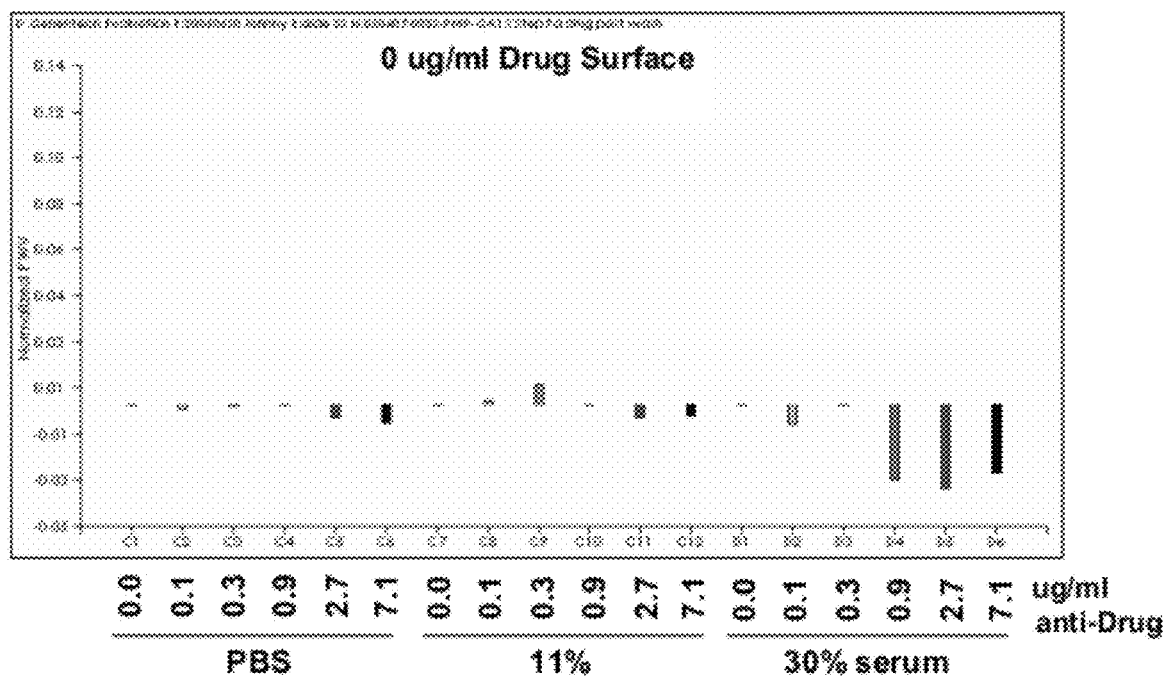

In one embodiment, the methods of the invention comprise the use of a biosensor that can be used to, inter alia, detect inorganic or organic material, such as protein, DNA, small molecules, viruses, cells, and bacteria, without the requirement of a detectable label, such as fluorescent or radioactive labels. Numerous suitable biosensors can be used in the methods of invention, including, but not limited to, photonic crystal biosensors (e.g., colorimetric resonant reflectance biosensors, silver nanoparticle array biosensors), interferometric biosensors (e.g., RIfS, dual polarization interferometer, Hartman Interferometer), MEMS biosensors (e.g., cantilevers, resonant membranes), acoustic biosensors (e.g., quartz resonator), microwave biosensors (e.g., dielectric spectroscopy), surface plasmon resonance (SPR) biosensors (e.g., kreitchman SPR biosensors, imaging SPR biosensors, grating coupled imaging SPR biosensors), waveguide biosensors (e.g., input grating coupler biosensors, chirped waveguide grating biosensors), evanescent wave-based biosensors and any biosensors incorporating an optical waveguide, as described for example in U.S. Pat. Nos. 4,815,843; 5,071,248; and 5,738,825; the disclosures of which are incorporated by reference in their entirety.

The methods of the invention have utility in, inter alia, the fields of pharmaceutical research (e.g., primary screening, high throughput screening, secondary screening, quality control, cytotoxicity, clinical trial evaluation), life science research (e.g., proteomics, protein interaction analysis, DNA-protein interaction analysis, enzyme-substrate interaction analysis, cell-protein interaction analysis), diagnostic tests (e.g., protein presence, cell identification), and environmental detection (bacterial and spore detection and identification).

Previous patent applications and publications describe how a colorimetric resonant reflectance biosensor surface, in combination with a high resolution imaging instrument, can be used as a platform for performing many biochemical assays in parallel upon on single surface, using only nanoliters of sample material. See, e.g., U.S. Pat. Publ. Nos.: 2002/0168295; 2002/0127565; 2004/0132172; 2004/0151626; 2003/0027328; 2003/0027327; 2003/017581; 2003/0068657; 2003/0059855; 2003/0113766; 2003/0092075; 2003/0026891; 2003/0026891; 2003/0032039; 2003/0017580; 2003/0077660; 2004/0132214.

Colorimetric resonant reflectance biosensors comprise a subwavelength structured surface. Subwavelength structured surfaces are a type of diffractive optic that can mimic the effect of thin-film coatings. See, e.g., Peng & Morris, "Resonant scattering from two-dimensional gratings," *J. Opt. Soc. Am. A*, Vol. 13, No. 5, p. 993, May 1996; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996. A grating of a photonic crystal biosensor of the invention has a grating period that is small compared to the wavelength of incident light such that no diffractive orders other than the reflected and transmitted zeroth orders are allowed. A photonic crystal biosensor can comprise a grating, which is comprised of or coated with a high dielectric constant dielectric material, sandwiched between a substrate layer and a cover layer that fills the grating grooves. Optionally, a cover layer is not used. The grating structure selectively couples light at a narrow band of wavelengths. This highly sensitive coupling condition can produce a resonant grating effect on the reflected radiation spectrum, resulting in a narrow band of reflected or transmitted wavelengths. The depth and period of the grating are less than the wavelength of the resonant grating effect.

The reflected or transmitted color of a calorimetric resonant reflectance biosensors structure can be modified by the addition of molecules. The added molecules increase the optical path length of incident radiation through the biosensor structure, and thus modify the wavelength at which maximum reflectance or transmittance will occur.

When illuminated with white light a calorimetric resonant reflectance biosensor reflects only a single wavelength or a narrow band of wavelengths. When molecules are attached to the surface of the biosensor, the reflected wavelength (color) is shifted due to the change of the optical path of light that is coupled into the grating. By immobilizing molecules, such as specific binding substances to a biosensor surface, complementary binding partner molecules can be detected without the use of any kind of detectable label, e.g., a fluorescent probe or particle label. The detection technique can be performed with the biosensor surface either immersed in fluid or dried.

When a colorimetric resonant reflectance biosensor is illuminated with collimated white light and reflects only a narrow band of wavelengths, or a single band of wavelengths is reflected. The narrow wavelength band is described as a wavelength "peak." The "peak wavelength value" (PWV) changes when molecules are deposited or removed from the biosensor surface. A readout instrument illuminates distinct locations on the biosensor surface with collimated white light, and collects collimated reflected light. The collected light is gathered into a wavelength spectrometer for determination of PWV.

Evanescent wave-based biosensors can comprise a waveguiding film supported by a substrate; between the waveguiding film (and optionally as part of the substrate) is a diffraction grating. See, e.g., U.S. Pat. No. 4,815,843. A low-k dielectric material, such as low-k nanoporous material can be used for the diffraction grating or the combined low-k nanoporous material and substrate. The waveguide comprises waveguiding film and the substrate. The waveguiding film can be, e.g., tin oxide, tantalum pentoxide, zinc sulfide, titanium dioxide, silicon nitride, or a combination thereof, or a polymer such as polystryrole or polycarbonate. A diffraction grating exists at the interface of the waveguiding film and the substrate or in the volume of the waveguiding film. The diffraction grating comprises a low-k material, such as low-k nanoporous material. The refractive index of the waveguiding film is higher than the index of the adjacent media (i.e., the substrate and the test sample). The substrate can be, e.g., plastic, glass or epoxy. A specific binding substance can be immobilized on the surface of the waveguiding film and a test sample added to the surface. Laser light propagates in the waveguiding film by total internal reflection. Changes in refractive index of the waveguiding film caused by molecules binding to it can be detected by observing changes in the angle of the emitted, out-coupled light.

A biosensor of the invention can comprise an inner surface, for example, a bottom surface of a liquid-containing vessel. A liquid-containing vessel can be, for example, a microtiter plate well, a test tube, a petri dish, or a microfluidic channel. One embodiment of this invention is a biosensor that is incorporated into any type of microtiter plate. For example, a biosensor can be incorporated into the bottom surface of a microtiter plate by assembling the walls of the reaction vessels over the resonant reflection surface, so that each reaction "spot" can be exposed to a distinct test sample. Therefore, each individual microtiter plate well can act as a separate reaction vessel. Separate chemical reactions can, therefore, occur within adjacent wells without intermixing reaction fluids, and chemically distinct test solutions can be applied to individual wells.

The most common assay formats for pharmaceutical high-throughput screening laboratories, molecular biology research laboratories, and diagnostic assay laboratories are microtiter plates. The plates are standard-sized plastic cartridges that can contain 96, 384, or 1536 individual reaction vessels arranged in a grid. Due to the standard mechanical configuration of these plates, liquid dispensing, robotic plate handling, and detection systems are designed to work with this common format. A biosensor of the invention can be incorporated into the bottom surface of a standard microtiter plate. Because the biosensor surface can be fabricated in large areas, and because the readout system does not make physical contact with the biosensor surface, an arbitrary number of individual biosensor areas can be defined that are only limited by the focus resolution of the illumination optics and the x-y stage that scans the illumination/detection probe across the biosensor surface.

Phage Preparations

Phage are bacterial viruses and are species specific. For this particular discussion, two *Escherichia coli* phage, M13 and Lambda, are being discussed. In the case of other bacterial phage and/or mammalian viruses the same premise applies. A population of phage, in particular, a non-homogenous, crude, and/or unconcentrated population of phage, such as a phage display library can be used in methods of the invention. A non-homogenous preparation of phage comprises a preparation that contains one or more type of phage, e.g., a phage display library wherein each phage displays a different binding molecule. A crude phage preparation is a preparation that contains one or more types of phage in the medium in which bacteria infected with phage was grown in. In the case of M13, the phage fuse through the membrane and the cell is not lysed. In the case of lambda, the cells are lysed and the medium would contain cellular components. In this case the crude phage preparation would be clarified of bacterial cells and membrane components by centrifugation. A crude phage preparation contains one or more types of phage at low concentrations in the presence of media components and excreted cellular catabolites.

An unconcentrated phage preparation is a phage preparation where the phage has not been precipitated. When the phage is precipitated, the medium is removed and the phage can be resuspended in a defined buffer such as PBS. During the purification process of M13 phage, the phage is usually precipitated with a PEG solution one or two times and is stored in PBS glycerol. During the process the phage is resuspended in smaller volumes of buffer than the original volume of medium. A typical 1-2 liter culture of medium will be resuspended in a final volume of about 2-5 ml of PBS, providing a purified and concentrated stock of phage.

Immobilization of Phage

A phage preparation is immobilized to a biosensor. A phage preparation can be passively immobilized to a biosensor surface. The phage surface can be blocked and an antigen (e.g. small molecule, carbohydrate, polymer, peptide, soluble protein, antigen mimic of a cellular receptor, or mammalian cells) can be screened for binding to the immobilized phage. The binding of the antigen specifically to the phage is measured by the change in signal generated by such a binding event, typically via optical, electrical or visual means. Antigen binding to the phage can be ranked by concentration of the phage, off-rate of the antigen, and the ability of the phage to functionally bind cells.

A phage preparation can be immobilized to a biosensor surface using specific antibody immobilization. An antibody to a phage coat protein is immobilized to the biosensor surface. The antibody can be passively immobilized to the biosensor surface or via a specific surface such as protein A or a protein A plus anti-Fc surface. The surface can be blocked by a blocker. The binding of the phage specifically to the surface is measured by the change in signal generated by such a binding event, typically via optical, electrical or visual means. The display on the phage (virus) can be a peptide, small protein, and/or an antibody fragment or non-existent. The binding of the cognate ligand is then sequentially measured by the change in signal generated by such a binding event, typically via optical, electrical or visual means. The ligand can be, e.g., a small molecule, carbohydrate, polymer, peptide, soluble protein, antigen mimic of a cellular receptor or a protein on the surface of cells. The protein expressed on the surface of the cell can be, e.g., a membrane-associated protein, a single or multi-transmembrane protein, or a protein channel.

A phage preparation can be immobilized to a biosensor surface by an antigen bound to the biosensor surface. An antigen (such as a small molecule, carbohydrate, polymer, peptide, soluble protein, or antigen mimic of a cellular receptor) is immobilized on the biosensor surface in a passive or specific surface such as an antibody that does not interfere with the desired binding epitope being screened. The antigen surface can be blocked. The binding of the phage preparation specifically to the antigen is measured by the change in signal generated by such a binding event, typically via optical, electrical or visual means. The display on the phage can be, e.g., a peptide, small protein, and/or an antibody fragment. Phage binding to the antigen can be ranked by concentration of the antigen, and the off-rate of the phage.

Antibody fragments (and proteins) can be captured specifically to the surface of the biosensor through biotin or proteinaceous tags (multiple histidines, c-myc, or FLAG, MBP, GST_etc.) fused to their N- or C-terminal domains. A specific surface can be built on the biosensor based on antibodies to the tags. Alternatively, antibody fragments can be captured specifically through the constant region (CH1). A specific surface can be built on the biosensor based on antibodies to this region using anti-lambda, anti-kappa, a mixture of anti-lambda and anti-kappa, and/or anti-F(ab')$_2$ antibodies. The surface can be blocked. The binding of the antibody fragment specifically to the antibody is measured by the change in signal generated by such a binding event, typically via optical, electrical or visual means. The immobilization of the antibody fragment can be from a pure or crude (whole cell extract, periplasmic extract, or spent media) sample. The binding of the cognate ligand can then be sequentially measured by the change in signal generated by such a binding event, typically via optical, electrical or visual means. The ligand can be, e.g., a small molecule, carbohydrate, polymer, peptide, soluble protein, antigen mimic of a cellular receptor or a protein on the surface of cells. The protein expressed on the surface of the cell can be, e.g., a membrane-associated protein, a single or multi-transmembrane protein, or a protein channel.

While it is not necessary for specific binding substances or binding partners to comprise a detectable label, detectable labels can be used to detect specific binding substances or binding partners on the surface of a biosensor. Where specific binding substances and binding partners of the instant invention are free of detection labels, they can still comprise other types of labels and markers for enhancement of assay sensitivity, immobilization of specific binding partners to a biosensor surface, enhancement of binding or hybridization of specific binding substances to their binding partners, and for other purposes.

Molecules can be immobilized onto a biosensor so that they will not be washed away by rinsing procedures, and so that binding to molecules in a test sample is unimpeded by the biosensor surface. Several different types of surface chemistry strategies have been implemented for covalent attachment of molecules to, for example, glass for use in various types of microarrays and biosensors. These same methods can be readily adapted to a biosensor of the invention.

One or more types of molecules can be attached to a biosensor surface by physical adsorption (i.e., without the use of chemical linkers) or by chemical binding (i.e., with the use of chemical linkers). Chemical binding can generate stronger attachment of molecules on a biosensor surface and provide defined orientation and conformation of the surface-bound molecules.

Other types of chemical binding include, for example, amine activation, aldehyde activation, and nickel activation. These surfaces can be used to attach several different types of chemical linkers to a biosensor surface. While an amine surface can be used to attach several types of linker molecules, an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal Chem.* 68, 490, (1996)).

Immobilization of specific binding substances to plastic, epoxy, or high refractive index material can be performed essentially as described for immobilization to glass. However, an acid wash step can be eliminated where such a treatment would damage the material to which the specific binding substances are immobilized.

Antigens

One or more specific binding substances can be immobilized on a biosensor by for example, physical adsorption or by chemical binding. A specific binding substance can be, for example, an organic molecule, such as a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, phage, bacteria, polymer, peptide solutions, single- or double-stranded DNA solutions, RNA solutions, solutions containing compounds from a combinatorial chemical library, or biological sample; or an inorganic molecule. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid. Preferably, an antibody, an antibody fragment, an antigen, or a phage is immobilized on a biosensor. Such specific binding substances can be directly immobilized as described herein, or can be indirectly immobilized via a specific surface. For example, an antibody or protein comprising a proteinaceous tag (e.g. histidines, c-myc, or FLAG, MBP, GST etc.) can be immobilized to a biosensor via an antibody that binds the tag. A binding partner is a substance that specifically binds to a specific binding substance. A binding partner can be any type of sample or molecule as described above for specific binding substances.

Methods

The methods of the invention can be used, for example, in: development of therapeutic and diagnostic antibodies by screening hybridomas, human antibodies from mice and phage display technologies; screening mRNA T7 phage display libraries; and a mammalian and bacterial cell free system for titration of bacterial as well as mammalian viruses. In this document binding molecules will be discussed, in particular, antibody fragments and/or full antibodies, eg. FIG. 1.

Applications for Viruses and Phage

The method of the invention can be used to titrate viruses. Typically, titration of viruses requires live mammalian and bacterial cells for mammalian and bacterial viruses, respectively. The circles of death or slower growing cells are counted. Using methods of the invention antibodies to the coat protein of the mammalian or bacterial virus are attached to the biosensor and dilutions of intact virus are detected via the antibody and coat protein interaction. In addition, M13 phage can be titrated by direct immobilization of the phage using a GA3 high density gluteraldehyde biosensor, see eg. FIG. 2. The GA3 biosensor was hydrated with PBS for 30 minutes, then purified M13 in 20% glycerol were prepared using 1:2 serial dilutions from 1.0e14 to 1.3e11 plaques per ml and were added to the sensor in 20% glycerol and PBS. The phage solutions were incubated with the sensor for 2 hours. The unbound phage were washed away and an endpoint reading was recorded for the amount of phage immobilized via the free amines on the phage protein coat.

Methods of the invention can also be used in the investigation of the biology (receptor binding, entry into cells, screening of neutralizing antibodies, etc.) surrounding mammalian viruses. For example, a virus is immobilized on the biosensor and antibodies or proteins are screened for their ability to increase or decrease the fusion of the virus to the mammalian cells.

The methods of the invention can also be used to detect toxins, viruses, and other bio-terrorism agents. For example, one can pan against targets, such as known toxins, virus, and other bio-terrorism agents or antigens derived from them with a phage display library. These libraries can display peptides, antibody fragments, protein scaffolds, or protein domains. During the panning process, phage are enriched for the ability to bind the target. During the screening process of the phage, lead candidates are identified. At this point, methods of the invention can be used to detect the toxins, virus, or other bio-terrorism agents by immobilizing the phage to the biosensor. This would replace the cumbersome work of synthesizing the peptide or performing molecular cloning of the protein or antibody fragments that are displayed on the phage.

Methods of the invention can be used for screening (after a phage panning or selection experiment) a large number of potential binding display phage for positive binding. Due to the ability to create specific binding surfaces, phage can be specifically pulled out of defined and undefined solutions, such as bacterial extracts and spent media and immobilized on a biosensor.

Methods of the invention can also be used to rank antibody affinities early at the phage level of screening, when using phage display technologies to identify therapeutic or diagnostic antibodies. For example, a phage displaying an antibody fragment can be immobilized to the biosensor directly or via an antibody to the coat protein. A signal for the amount of phage immobilized per well is recorded. The antigen for the antibody displayed on the phage is added and a signal is recorded. A rank can be determined by dividing the signal/well for antigen by the signal/well for the phage. By this calculation the antigen signal is normalized for units of phage in each assay (well). The antibody fragment on the phage could be ranked for its monovalent affinity without the use of molecular biology techniques to clone the gene for the antibody fragment. This technique would enable ranking of antibody fragments with out the need for cloning the gene, expression of the antibody fragment, purification of the antibody fragment, then ranking of binding with the antigen.

Methods of the invention can be used to determine the off-rate of the display on a phage for the corresponding antigen. For example, a phage is immobilized on a biosensor, washed, and antigen is bound. After each wash sequence, the biosensor is read. If the antigen is released from the phage on the biosensor, then there is a loss in signal. The biosensor is monitored over multiple washes and the off-rate is calculated as the loss of signal over time.

Binding partners can be identified using this technology, by binding cellular components to the biosensor, then adding protein partners or phage containing DNA sequences corresponding to cellular components. A test sample, such as cell lysates containing binding partners, can be applied to a biosensor of the invention, followed by washing to remove unbound material. The binding partners that bind to a biosensor can subsequently be eluted from the biosensor and identified by, for example, mass spectrometry. A phage DNA display library can be applied to a biosensor of the invention followed by washing to remove unbound material. Individual phage particles bound to the biosensor can be isolated and the inserts in these phage particles can then be sequenced to determine the identities of the binding partners. Antibodies can be immobilized in an array format onto a biosensor, which is then contacted with a test sample of interest comprising binding partners, such as proteins. Only the proteins that specifically bind to the antibodies immobilized on the biosensor remain bound to the biosensor. Such an approach is essentially a large-scale version of an enzyme-linked immunosorbent assay; however, the use of an enzyme or fluorescent label is not required.

The methods of the invention provide several advantages over conventional phage display and phage panning protocols, including, for example: (1) label free and direct binding of the display on the phage immobilized on the biosensor to cells or other binding partners is not influenced by protein labels and amplification of secondary signals; (2) specific pull down of phage (i.e., immobilization of phage to a biosensor) from crude samples and the binding of cells or other binding partners without excessive washing detects functional binding of mammalian cells faster; and (3) high throughput, thereby providing the most efficient and rapid phage screening methods.

In addition, conventional protocols using phage display to determine functional binding of antibodies to mammalian cells requires a considerable amount of time and effort in cloning the display on the phage to fragments and/or full IgGs in order to investigate the functional binding to cells. The methods of the invention simplify the process by eliminating the need to purify phage and are amenable to high throughput screening as described herein. Thus, the methods of the invention as described herein provide the benefit of allowing a researcher to go from the phage panning experiment directly to testing the functional activity of the display on mammalian cells (the functional antigen). In particular, since the methods of the invention are high throughput, cellular binding can be investigated in the first binding experiment rather than later as in a conventional discovery pipeline. As the binding to cells is the crucial assay for identifying a therapeutic antibody, the methods of the invention enable a researcher to acquire critical information early, thereby accelerating therapeutic discoveries. In many cases the methods of the invention could save discovery researchers up to three to six months of effort in identifying therapeutic antibodies.

For the above applications, and in particular proteomics applications, the ability to selectively bind material, such as binding partners from a test sample onto a biosensor of the invention, followed by the ability to selectively remove bound material from a distinct location of the biosensor for further analysis is advantageous. Biosensors of the invention are also capable of detecting and quantifying the amount of a binding partner from a sample that is bound to a biosensor array distinct location by measuring the shift in reflected wavelength of light. Additionally, the wavelength shift at one distinct biosensor location can be compared to positive and negative controls at other distinct biosensor locations to determine the amount of a binding partner that is bound to a biosensor array distinct location.

Applications for IgGs and Antibody Fragments

Methods of the invention can be used to capture antibodies and antibody fragments, from complex media such as, e.g., periplasmic extracts, hybridoma supernatants, plasma, or sera. See, e.g., FIGS. 3 to 10. The following specific surface can be modified to capture full IgGs or F(ab) by substituting rabbit anti-mouse-Fc, rabbit anti-human Fc, rabbit anti-human F(ab')2, or the rabbit anti-mouse-F(ab')2 in the following example. The following procedure is for the capture of sF(ab) spiked into PBS and periplasmic cultures described in FIG. 3. A specific capture surface for sFab was created on a SRU BIND® TIO Biosensor, FIG. 3(A). A hydrated TIO BIND® Biosensor was coated with 20 ug/ml Protein A in PBS for 30 minutes, washed and an endpoint reading was recorded for the amount of protein A deposited. The Biosensor was then blocked for 30 minutes with 1% milk, washed and an endpoint reading was recorded for the amount of milk deposited. Then 20 ug/ml of the specific capture reagent, rabbit anti-mouse F(ab')2 specific IgG, was incubated for 30 minutes, washed, and an endpoint reading was recorded for the amount of rabbit anti-mouse F(ab')2 specific IgG deposited. The remaining protein A sites were blocked with 50 ug/ml rabbit IgG for 30 minutes. At this point a specific capture surface for mouse sF(ab) has been created. In this example, purified polyclonal mouse sF(ab), 0.33, 1.0 and 3.0 ug/ml, were spiked into PBS and into a Escherichia coli periplasmic prep, not expressing sF(ab), FIGS. 3(A) and 4(B).

FIG. 4 shows scFv capture from periplasmic extract on a TIO BIND® Biosensor. A hydrated TIO BIND® Biosensor was coated with 20 ug/ml Protein A in PBS for 30 minutes, washed and an endpoint reading was recorded for the amount of protein A deposited. The Biosensor was then blocked for 30 minutes with 1% milk, washed and an endpoint reading was recorded for the amount of milk deposited. Then 20 ug/ml of the specific capture reagent, rabbit anti-mouse-Fc, was incubated for 30 minutes, washed, and an endpoint reading was recorded for the amount of rabbit anti-mouse-Fc specific IgG deposited. Two capture antibody surfaces were created, (1) 25 ug/ml anti-his and 25 ug/ml anti-cmyc and (2) 50 ug/ml anti-cmyc, incubated for 30 minutes, washed, and an endpoint reading was recorded for the amount of capture antibodies deposited. At this point a scFv capture surface has been created, FIG. 4(A). Purified scFv (5 ug/ml) were spiked into PBS and periplasmic extracts of Escherichia coli, not containing plasmids encoding scFv. The scFv were incubated for 1 hour, washed, and an endpoint reading was recorded for the amount of scFv deposited. The amount of scFv is tabulated in FIG. 4(B) and graphically represented in FIGS. 4(C) and 4(D).

FIG. 5 shows scFv capture from periplasmic extract on a SA1 BIND® Biosensor. A hydrated SA1 BIND® Biosensor, streptavidin, was incubated with 50 ug/ml biotin anti-his for one hour, washed, and an endpoint reading was recorded for the amount of biotin-anti-his deposited FIG. 5(A). Eight micrograms per milliliter of scFv was spiked into PBS and periplasmic extracts of Escherichia coli, not containing plasmids encoding scFv. The scFv were incubated for 1 hour, washed, and an endpoint reading was recorded for the amount of scFv deposited. The amount of scFv is tabulated in FIG. 5(B) and graphically represented in FIG. 5(C).

FIG. 6 shows scFv capture from periplasmic extract on a GA1 BIND® Biosensor. A hydrated GA1 BIND® Biosensor, gluteraldehyde, was incubated with 50 ug/ml anti-cmyc for one hour, washed, and an endpoint reading was recorded for the amount of anti-myc deposited, FIG. 6(A). Two hundred micrograms per milliliter of neutravidin was incubated with the BIND® Biosensor to block any remaining gluteraldehyde reactive groups for 1 hour, washed, and an endpoint reading was recorded for the amount of neutravidin deposited. Five micrograms per milliliter of scFv was spiked into PBS and periplasmic extracts of Escherichia coli, not containing plasmids encoding scFv. The scFv were incubated for 1 hour, washed, and an endpoint reading was recorded for the amount of scFv deposited. The amount of scFv is tabulated in FIG. 6(B) and graphically represented in FIG. 6(C).

In FIG. 7, mouse IgGs created via hybridoma technologies are captured from hybridoma supernatants then tested for their ability to bind soluble antigen and antigen expressed on cells. A specific capture surface for mouse IgG was created on a SRU BIND® TIO Biosensor, FIGS. 7(A) and 7(B). A hydrated TIO BIND® Biosensor was coated with 20 ug/ml Protein A in PBS for 30 minutes, washed and an endpoint reading was recorded for the amount of protein A deposited. The biosensor was then blocked for 30 minutes with 1% milk, washed and an endpoint reading was recorded for the amount of milk deposited. Then 20 ug/ml of the specific capture reagent, rabbit anti-mouse Fc specific IgG, was incubated for 30 minutes, washed and an endpoint reading was recorded for the amount of rabbit anti-mouse Fc specific IgG deposited. The remaining protein A sites were blocked with 50 ug/ml rabbit IgG for 30 minutes. At this point a specific capture surface for mouse IgG has been created. Plate 15 was used to test binding of antigen expressing transfected cell line and the parental cell line. Plate 16 was used to test antigen binding. FIG. 7(C) shows the shift in nm measured for the capture of mouse IgGs from hybridoma supernatants on Plate 15 and Plate 16. FIG. 7(D) shows the antigen and cell binding to the captured IgGs on the BIND® Biosensors. FIG. 7(E) shows the nm shifts for the antigen and cell binding as well as the ratio of antigen signal divided by the IgG signal and the ratio of the cell binding signal divided by the IgG signal. These ratios can be used to rank the IgGs. Antibodies 22, 25, 26, 28, 30, 31, 34, 36 and 37 can be classified as antigen binders (antigen binding divided by IgG binding) with 37 having the highest affinity for the antigen with a ratio of 0.13. Antibodies 22, 25, and 26 have similar affinities and constitute the second class of binders with a ratio of 0.10. The remaining antibodies (28, 30, 31, 34 and 36) have much lower affinities with their ratio less than 0.04. The IgGs can also be classified as a general cell binder in the case of antibody 30 with a ratio for the parental cell line divided by IgG of 0.11 and the antigen presenting cells divided by IgG of 0.16. The second cell binding class would be specific for antigen expressed on the cells as in the antibodies 25 and 26 with ratios for the antigen presenting cells divided by IgG of 0.49 and 0.30, respectively, and the parental cell line divided by IgG of 0.00 and 0.01, respectively. The rest of the antibodies are non-cell binders with ratios for binding the parental cell line divided by IgG and the antigen presenting cells divided by IgG less than 0.04.

FIG. 8 shows antibody capture from serum using an anti-Fc TIO BIND® Biosensor. A specific capture surface for mouse IgG was created on a SRU BIND® TIO Biosensor FIG. 8(A). A hydrated TIO BIND® Biosensor was coated with 20 ug/ml Protein A in PBS for 30 minutes, washed and an endpoint reading was recorded for the amount of protein A deposited. The Biosensor was then blocked for 30 minutes with 1% milk, washed and an endpoint reading was recorded for the amount of milk deposited. Then 20 ug/ml of the specific capture reagent, rabbit anti-mouse Fc, was incubated for 30 minutes, washed and an endpoint reading was recorded for the amount of rabbit anti-mouse Fc deposited. The remaining protein A sites were blocked with 50 ug/ml rabbit IgG for 30 minutes. At this point a specific capture surface for mouse IgG has been created. FIGS. 8(B) and (C) shows the capture of mouse IgG (serial dilution from 0.1-6.4 ug/ml) that were spiked into PBS and 5%, 10%, 20%, 40% and 100% serum.

FIG. 9 shows the Drug—anti-Drug assay in serum using a GA1 Bind Biosensor. An IgG is the mimic for a therapeutic antibody drug and the anti-Drug is a F(ab')2 spiked into PBS and mouse sera to mimic IgGs found in human sera from clinical isolates using a GA1 BIND® Biosensor. A hydrated GA1 BIND® Biosensor was incubated with 20 ug/ml IgG for 1 hour, washed and an endpoint reading was recorded for the amount IgG deposited on the surface. The free aldehydes remaining on the surface of the GA1 BIND® Biosensor were bound up by incubating the sensor with 100 ug/ml non-immune rabbit IgG for 2 hours. The IgG (Drug):rIgG surface was also blocked by START Block from Pierce for 1 hr. FIG. 9(A) shows the nm shifts for the production of a drug surface specific. A titration curve of anti-Drug from 0-7.1 ug/ml was incubated on the Biosensor by diluting the anti-drug in serial 1:3 dilutions into PBS or 11%, and 30% mouse serum. The binding of anti-Drug to the 20 ug/ml, FIG. 9(B) and to 0 ug/ml Drug surface, FIG. 9(C) is represented in graphs. The same amount of anti-drug is captured in 11% serum compared to PBS. Less anti-Drug is captured in 30% serum, but the anti-Drug is detectable.

Figure 10C:
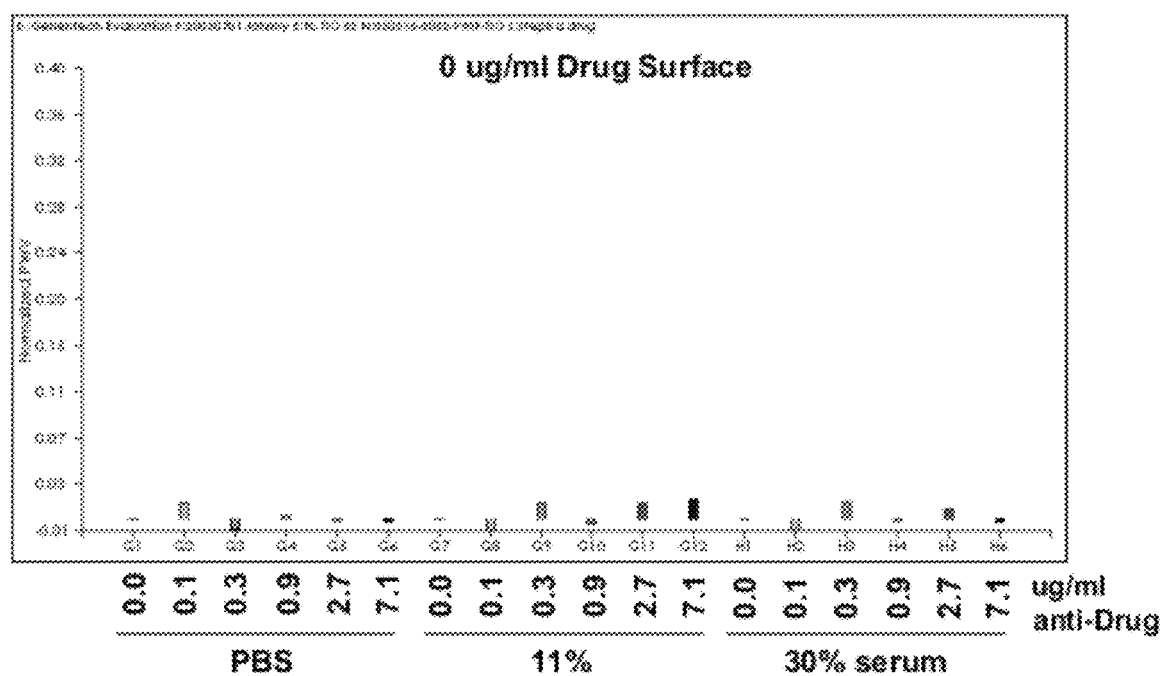

FIG. 10 shows the development of a Drug—anti-Drug assay in serum using a TIO BIND® Biosensto. An IgG is the mimic for a therapeutic antibody drug and the anti-Drug is a F(ab')2 spiked into PBS and mouse sera to mimic IgGs found in human sera from clinical isolates. FIG. 10(A) shows the shifts measured during the creation of a specific surface for the capture of mouse IgGs. A hydrated TIO BIND® Biosensor is coated with 20 ug/ml of protein A. One percent milk is used to block any remaining binding sites on the TIO not filled by protein A. After the milk blocking step the surface is incubated with 20 ug/ml rabbit anti-human-Fc. Rabbit IgG at 50 ug/ml is used to block any protein A binding sites not filled by the rabbit anti-mouse-Fc. During this stage of the experiment each reagent is incubated with the surface for thirty minutes, the surface is washed and an endpoint reading was recorded for the amount of each reagent deposited on the surface. Fifty micrograms per milliliter of Drug (IgG) was incubated with the specific surface for 1 hour, washed and an endpoint reading was recorded for the amount of each Drug deposited on the surface. A titration curve of anti-Drug from 0-7.1 ug/ml was incubated on the Biosensor by diluting the anti-drug in serial 1:3 dilutions into PBS or 11%, and 30% mouse serum. The binding of anti-Drug to the 50 ug/ml and 0 ug/ml Drug surface is shown in FIGS. 10(B) and 11(C), respectively. Less anti-Drug is captured in 11% and 30% serum, but the anti-Drug is detectable.

Determination of Epitope Classes within an Antibody Screen

Epitope classes within an antibody screen (antibody or antibody fragment) or a phage screen can be determined using methods of the invention. In the example, the binding molecules to be classified can be antibodies or display phage or a combination of both. The first binding molecule is passively or specifically immobilized to a biosensor. Preferably, the biosensor comprises the bottom surface of a microtiter plate. The surface can be blocked by blockers. An antigen (such as a carbohydrate, polymer, peptide, soluble protein, or antigen mimic of a cellular receptor) is captured specifically by the display phage, antibody, or antibody fragment surface. Individual phage clones, antibodies, or antibody fragments to be classified are added to the wells. Where the display phage, antibody, or antibody fragment immobilized in the wells bind within the same epitope class as the phage, antibody or antibody fragment to be classified, there would not be a measurable signal as the binding sites are filled via the immobilized phage, antibody or antibody fragment. Where the display phage, antibody, or antibody fragment immobilized in the wells recognize different epitope binding sites than the phage, antibody or antibody fragment to be classified then a measurable signal would be recorded.

FIG. 11 shows an endpoint analysis of monoclonal antibody binding target peptides for epitope mapping using a calorimetric resonant reflectance biosensor. FIG. 11(A) shows the shifts measured during the creation of a specific surface for the capture of mouse IgGs. A hydrated TIO BIND® Biosensor is coated with 20 ug/ml of protein A. The protein A acts as a capture surface for the rabbit anti-mouse-Fc that will specifically captures mouse IgGs. One percent milk is used to block any remaining binding sites on the TIO not filled by protein A. After the milk blocking step the surface is incubated with 20 ug/ml rabbit anti-mouse-Fc. Rabbit IgG at 50 ug/ml is used to block any protein A binding sites not filled by the rabbit anti-mouse-Fc. During this stage of the experiment each reagent is incubated with the surface for thirty minutes, the surface is washed and an endpoint reading was recorded for the amount of each reagent deposited on the surface. In FIG. 11(B), the capture of the four mouse IgGs by the protein A:milk:rabbit anti-mouse-Fc:rabbit IgG surface is recorded. Ten micrograms per milliliter of IgGs were incubated with the specific surface for 30 minutes. To ensure that the second layer of mouse IgGs bind through the antigen and not the rabbit anti-mouse-Fc, non-immune mouse IgG from Pierce is added at 50 ug/ml to fill any unoccupied rabbit anti-mouse-Fc binding sites, FIG. 11(A). FIG. 11(C) records the shift measured when antigen is added to captured mouse IgG. Ab-4 does not bind antigen and the 4 IgGs can be classified as antigen binders (Ab-1, Ab-2 and Ab-3) and antigen non-binders (Ab-4). The antigen binding antibodies can also be ranked by dividing the antigen shift by the antibody shift measured by the BIND® Biosensor. Ab-2 has the highest affinity for antigen with a ratio of 0.56. Ab-3 has a slightly higher affinity for the antigen than Ab-1 with ratios of antigen binding per antibody shift of 0.38 and 0.35, respectively. FIG. 11(D) shows the grid created by the addition of the same mouse IgGs in layer 1 as layer 3. If two IgGs in the same well bind the same area of the antigen, then no signal will be measured. This is exemplified by the addition of the same antibody into the same well twice. Self competition results in no signal as seen on the diagonal: Ab-1 vs. Ab-1 results in 0.016 nm; Ab-2 vs. Ab-2 results in 0.063 nm; and Ab-3 vs. Ab-3 results in 0.050 nm. Ab-1 and Ab-3 are in the same binding class and cannot be used as a sandwich pair as Ab-1 vs Ab-3 results in 0.033 nm shift and reverse orientation of Ab-3 vs. Ab-1 results in 0.024 nm shift. If the two IgGs in a well are both able to bind the antigen simultaneously, then they belong to different binding classes and can be used as a sandwich pair. Ab-2 is in a second binding class and can be used as a sandwich partner for both Ab-1 and Ab-3: Ab-1 vs. Ab-2 equals 0.138; Ab-2 vs. Ab-1 equals 0.150; Ab-3 vs. Ab-2 equals 0.203; and Ab-2 vs. Ab-3 equals 0.212. This technique will work where the first and/or the second antibody immobilized are a displayed on phage or a soluble antibody (purified or crude sample). Combinations include phage:phage, phage:antibody fragment, antibody fragment:phage, antibody fragment:antibody fragment, full antibody:phage, phage:full antibody, full antibody:full antibody, antibody fragment:full antibody, and antibody:antibody fragment. This can also be applied to hybridoma and phage display screens as well as human antibodies made in other hosts, such as mice.

All patents, patent applications, and other scientific or technical writings referred to anywhere herein are incorporated by reference in their entirety. The methods and compositions described herein as presently representative of preferred embodiments are exemplary and are not intended as limitations on the scope of the invention. Changes therein and other uses will be evident to those skilled in the art, and are encompassed within the spirit of the invention. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

What is claimed is:

1. A method for detecting if different epitope classes of antibodies in an antibody population are present as compared to display phage, antibodies, or antibody fragments immobilized on a biosensor comprising:
    (a) immobilizing display phage, antibodies, or antibody fragments to a biosensor;
    (b) contacting the biosensor with a binding partner that specifically binds to the display phage, antibodies, or antibody fragments immobilized to the biosensor, under conditions suitable for binding of the binding partner to the display phage, antibodies, or antibody fragments;
    (c) contacting the antibody population with the biosensor; wherein, a detectable signal generated by binding of the antibody population to the binding partner indicates that different epitope classes are present in the antibody population than in the immobilized display phage, antibodies, or antibody fragments.

2. The method of claim 1, wherein the antibody population comprises phage clones.

3. The method of claim 1, wherein the antibody population comprises antibody fragments, full antibodies, phage displaying a full antibody, or phage displaying an antibody fragment.

4. The method of claim 1, wherein the antibody population comprises antibodies from a hybridoma.

5. The method of claim 1, wherein the antibody population comprises antibodies from a phage display screen.

6. The method of claim 1, wherein the display phage is a crude phage preparation, an unconcentrated phage preparation, a concentrated phage preparation or a non-homologous phage preparation.

7. The method of claim 1, wherein the binding partner is a small molecule, a carbohydrate, a polymer, a peptide, a soluble protein, a cellular receptor, an antigen mimic of a cellular receptor, a mammalian cell, or a mammalian cell surface protein.

8. The method of claim 7, wherein the mammalian cell surface protein is a membrane-associated protein, a single transmembrane protein, a multi-transmembrane protein, or a protein channel.

9. The method of claim 1, wherein the biosensor is a colorimetric resonant reflectance biosensor or an evanescent wave-based biosensor.

10. The method of claim 1, wherein the antibody population, binding partner and immobilized display phage, immobilized antibody, or immobilized antibody fragment do not comprise a detectable label.

11. The method of claim 1, wherein the display phage, antibodies, or antibody fragments are immobilized in an array format on the biosensor.

12. The method of claim 1, wherein the biosensor is incorporated into a bottom surface of a microtiter plate comprising wells, and wherein the display phage, antibodies, or antibody fragments are immobilized to the biosensor within each well.

13. The method of claim 1, where the method further comprises determining the quantity of binding partner bound to the phage immobilized on the biosensor.

14. The method of claim 1, wherein the biosensor is coated with streptavidin, amines, aldehydes or gluteraldehydes prior to the immobilization of the display phage, antibodies, or antibody fragments to the biosensor.

* * * * *